United States Patent
Bhushan et al.

(10) Patent No.: US 12,406,358 B2
(45) Date of Patent: Sep. 2, 2025

(54) METHODS AND SYSTEMS FOR AUTOMATED SATURATION BAND PLACEMENT

(71) Applicant: GE Precision Healthcare LLC, Wauwatosa, WI (US)

(72) Inventors: Chitresh Bhushan, Schenectady, NY (US); Dattesh Dayanand Shanbhag, Karnataka (IN); Soumya Ghose, Niskayuna, NY (US); Amod Suhas Jog, Karnataka (IN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 447 days.

(21) Appl. No.: 17/810,473

(22) Filed: Jul. 1, 2022

(65) Prior Publication Data

US 2024/0005480 A1    Jan. 4, 2024

(51) Int. Cl.
*G06T 7/00* (2017.01)
*G16H 30/40* (2018.01)

(52) U.S. Cl.
CPC ........... *G06T 7/0012* (2013.01); *G16H 30/40* (2018.01); *G06T 2207/20081* (2013.01); *G06T 2207/20084* (2013.01)

(58) Field of Classification Search
CPC ......... G06T 7/0012; G06T 2207/20081; G06T 2207/20084; G06T 7/75; G06T 7/11; G06T 2207/10088; G16H 30/40; G16H 40/67; G16H 50/20; G16H 50/70; G16H 30/20; G01R 33/4838; G01R 33/543; G01R 33/5608; G06N 3/0464; G06N 3/08
See application file for complete search history.

(56) References Cited

U.S. PATENT DOCUMENTS

| | | | | |
|---|---|---|---|---|
| 8,565,505 B2* | 10/2013 | Bergmans | ............ | G01R 33/543 600/407 |
| 8,929,638 B2* | 1/2015 | Dempsey | .................. | G06T 5/70 382/131 |
| 9,041,395 B2* | 5/2015 | Sorensen | ......... | G01R 33/56509 324/309 |

(Continued)

OTHER PUBLICATIONS

Khurd et al, Facilitating 3D Spectroscopic Imaging through Automatic Prostate Localization in MR Images Using Random Walker Segmentation Initialized via Boosted Classifiers (Year: 2011).*

(Continued)

*Primary Examiner* — Molly Wilburn
*Assistant Examiner* — Jordan McKenzie Elliott
(74) *Attorney, Agent, or Firm* — McCoy Russell LLP

(57) ABSTRACT

Methods and systems are provided for automatic placement of at least one saturation band on a medical image, which may direct saturation pulses during a MRI scan. A method may include acquiring a localizer image of an imaging subject, determining a plane mask for the localizer image by entering the localizer image as input to a deep neural network trained to output the plane mask based on the localizer image, generating a saturation band based on the plane mask by positioning the saturation band at a position and an angulation of the plane mask, and outputting a graphical prescription for display on a display device, the graphical prescription including the saturation band overlaid on the medical image.

9 Claims, 11 Drawing Sheets

(56) References Cited

U.S. PATENT DOCUMENTS

| | | | | |
|---|---|---|---|---|
| 2012/0197104 | A1* | 8/2012 | Posse | G01R 33/4838 |
| | | | | 600/410 |
| 2013/0245427 | A1* | 9/2013 | Rothgang | A61B 17/3403 |
| | | | | 600/411 |
| 2014/0058407 | A1* | 2/2014 | Tsekos | A61B 34/30 |
| | | | | 606/130 |
| 2018/0329007 | A1* | 11/2018 | Guo | G01R 33/4616 |
| 2020/0168320 | A1* | 5/2020 | Hu | G06N 3/045 |
| 2021/0080531 | A1* | 3/2021 | Gui | A61B 5/055 |
| 2022/0018922 | A1* | 1/2022 | Shim | G01R 33/4625 |
| 2022/0342018 | A1* | 10/2022 | Splitthoff | G01R 33/5676 |
| 2023/0067146 | A1* | 3/2023 | Truwit | A61B 5/7267 |
| 2024/0090791 | A1* | 3/2024 | Greiser | A61B 5/055 |

OTHER PUBLICATIONS

Salimi et al, ( Deep learning-based fully automated Z-axis coverage range definition from scout scants to eliminate over scanning in chest CT imaging, Published Nov. 6, 2021 (Year: 2021).*

Ozhinsky et al, Automated prescription of oblique brain 3D magnetic resonance spectroscopic imaging, Published Jun. 12, 2012 (Year: 2012).*

Ozhinsky, E. et al., "Improved Spatial Coverage for Brain 3D PRESS MRSI by Automatic Placement of Outer-Volume Suppression Saturation Bands," Journal of Magnetic Resonance Imaging, vol. 33, No. 4, Apr. 2011, 20 pages.

\* cited by examiner

METHODS AND SYSTEMS FOR AUTOMATED SATURATION BAND PLACEMENT

TECHNICAL FIELD

Embodiments of the subject matter disclosed herein relate to magnetic resonance imaging (MRI). In particular, the current disclosure provides systems and methods for placement of at least one saturation band on a localizer image based on anatomy present in the localizer image.

BACKGROUND

Magnetic resonance imaging (MRI) is a medical imaging modality that can create images of the inside of a human body without using x-rays or other ionizing radiation. MRI systems include a superconducting magnet to create a strong, uniform, static magnetic field $B_0$. When a human body, or part of a human body, is placed in the magnetic field $B_0$, the nuclear spins associated with the hydrogen nuclei in tissue water become polarized, wherein the magnetic moments associated with these spins become preferentially aligned along the direction of the magnetic field $B_0$, resulting in a small net tissue magnetization along that axis. MRI systems also include gradient coils that produce smaller amplitude, spatially-varying magnetic fields with orthogonal axes to spatially encode the magnetic resonance (MR) signal by creating a signature resonance frequency at each location in the body. The hydrogen nuclei are excited by a radio frequency signal at or near the resonance frequency of the hydrogen nuclei, which add energy to the nuclear spin system. As the nuclear spins relax back to their rest energy state, they release the absorbed energy in the form of an RF signal. This RF signal (or MR signal) is detected by one or more RF coils and is transformed into the image using reconstruction algorithms.

Saturation bands may be used in MRI to suppress an RF signal (or MR signal) from tissues outside of an imaging region of interest (e.g., an anatomy of interest). Prior to imaging, a saturation band may be prescribed to a localizer image and direct an imaging method or protocol to apply a saturation pulse to the region outlined by the saturation band when scanning for a diagnostic medical image. The saturation pulse may apply RF energy to suppress the MR signal from moving tissues outside of the imaged volume or to reduce and/or eliminate motion artifacts.

SUMMARY

The inventors herein have developed systems and methods which may enable automatic placement of at least one saturation band on a localizer image using a deep neural network, thereby enabling consistency and accuracy in saturation band placement. The current disclosure provides a method for acquiring a localizer image of an imaging subject, entering the localizer image as input to a deep neural network trained to output a plane mask based on the localizer image, generating a saturation band based on the plane mask, and outputting a graphical prescription for display on a display device, the graphical prescription including the saturation band overlaid on the localizer image. The plane mask may be a 3D projection which segments the localizer image as a binary plane mask, such that projecting the plane mask onto the localizer image provides lines on individual slides of localizer data, indicating a 3D plane of interest. In this way, anatomical information may be extracted from a 2D or 3D localizer image by leveraging the deep neural network, such as a convolutional neural network (CNN), to produce a plane mask for an anatomy of interest. The plane mask may then be used to determine a position and an orientation (e.g., an angulation) of a saturation band, which may be used along with user input to generate at least one saturation band. Generation and placement of the at least one saturation band on the localizer image using the CNN may facilitate patient evaluation and diagnosis while reducing a duration of saturation band placement prior to scanning.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
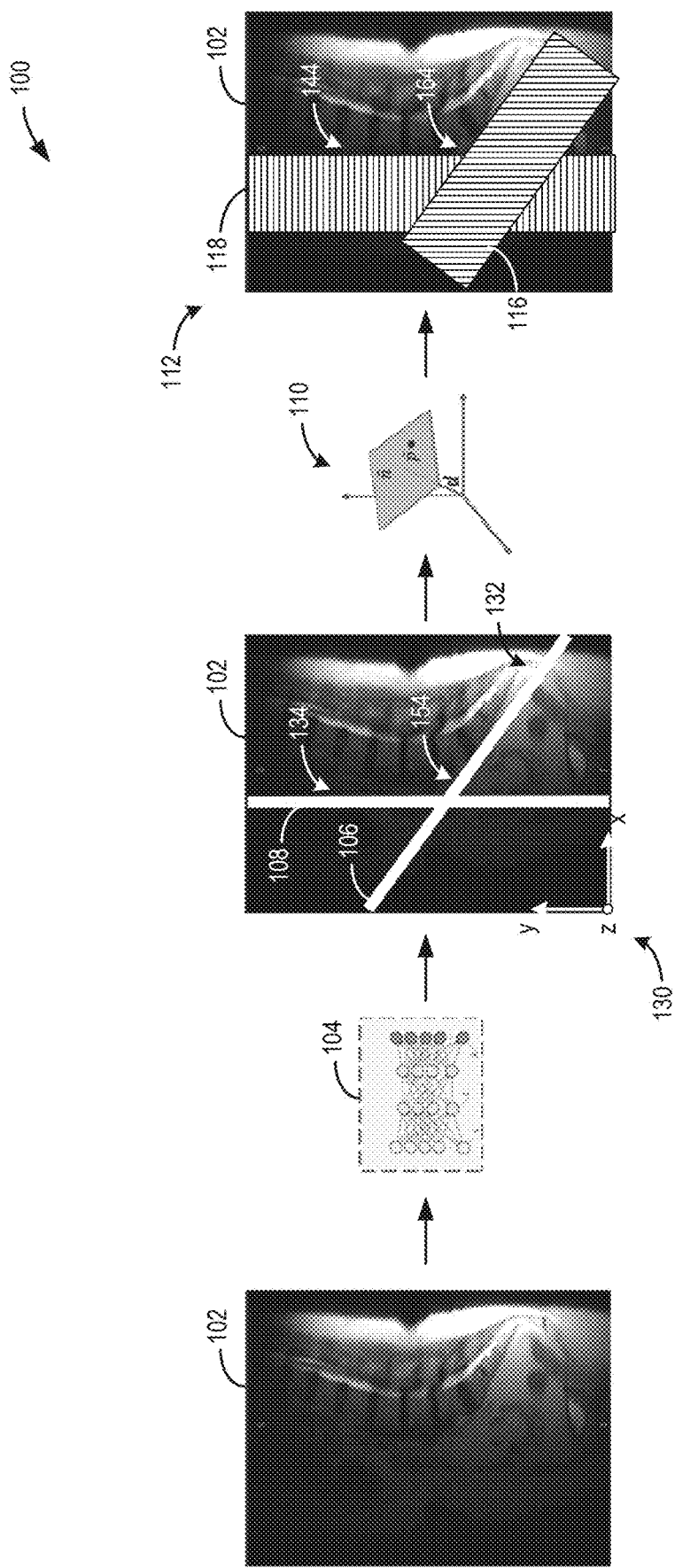
FIG. 1 is a workflow of a method for automatically prescribing at least one saturation band on a localizer image, according to an exemplary embodiment.

Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

The following description relates to automatic placement of at least one saturation band on a localizer image, based on at least one plane mask generated using a deep neural network. The disclosure includes aspects directed to generating training data for the deep neural network, training said deep neural network, as well as implementing the deep neural network to map the plane mask to the localizer image.

Saturation bands may be used in MRI to suppress an RF signal (or MR signal) from tissues outside of an imaging region of interest (e.g., an anatomy of interest). Prior to imaging, a saturation band may be prescribed to a localizer image and direct an imaging method or protocol to apply a saturation pulse to the region outlined by the saturation band when scanning for a diagnostic medical image. In some embodiments, the localizer image may be a low-resolution image which may include the same anatomy of interest as the diagnostic medical image but has a lower resolution, which may allow for less initial computing demand on an MRI apparatus. When scanning for the diagnostic medical image, the saturation pulse may apply RF energy to suppress the MR signal from moving tissues outside of the imaged volume or to reduce and/or eliminate motion artifacts. For example, for a localizer image where the anatomy of interest includes a spine, a saturation band may be prescribed on the localizer image to suppress chest wall and cardiac motion from "leaking" or otherwise overlapping signals into a spine region during subsequent acquisition of high resolution data (e.g., the diagnostic medical image). For an anatomy of interest including a lumbar spine region, two saturation bands may be prescribed on the respective localizer image: a first saturation band for a lumbar spine curvature (e.g., a first curvature) and a second saturation band for a sacral spine curvature (e.g., a second curvature). The first saturation band and the second saturation band may be positioned at different orientations (e.g., angles) which correspond to the respective curvature. When an anatomy of interest is a shoulder, an oblique saturation band may be prescribed over a chest region to reduce potential breathing artifacts during diagnostic medical image scanning. For time of flight angiography (TOF) imaging, a superior saturation band may be applied to the localizer image to suppress potential venous signal contamination. In some embodiments of pelvic region imaging, a tailored saturation band may be placed, where the tailored saturation band is placed along a posterior margin along a midline of a urinary bladder, and the tailored saturation band has a field-of-view length by one third of a maximum anteroposterior length of the pelvis. In magnetic resonance spectroscopy imaging (MRSI) of a brain, multiple localizer images may be prescribed over the patient's head to suppress lipid signals, thus multiple saturation bands may be prescribed.

Conventionally, a user such as an MRI technologist may manually prescribe at least one saturation band on a localizer image. For the scans described above (e.g., lumbar spine, shoulder, TOF, and so on), the MRI technologist may spend considerable time and effort determining regions of interest and prescribing at least one saturation band to suppress signals from outside the anatomy of interest. Herein described are systems and methods for automatic placement of at least one saturation band on a localizer image based on at least one plane mask generated using a deep neural network. The plane mask may be a 3D projection which segments the localizer image as a binary plane mask, such that projecting the plane mask onto the localizer image provides lines on individual slides of localizer data, indicating a 3D plane of interest. Generation of the at least one saturation band based on a corresponding plane mask of the at least one plane mask may account for patient position in 3D and allow consistent saturation band placement irrespective of patient position changes. For example, a position and an angulation of a plane mask which are determined to be sufficient parameters for saturation band placement may still allow for sufficient suppression of signals when used to position the saturation band in circumstances where an imaging subject has changes positions. This may allow for consistent imaging data to be generated over multiple scans longitudinally. The disclosure includes aspects directed to generating training data for the deep neural network, training said deep neural network, as well as implementing the deep neural network to map the plane mask to the localizer image. Automatic placement of the at least one saturation band using the methods described herein may reduce a time used to prescribe saturation bands (e.g., compared to manual prescription by a user), which may reduce an overall imaging duration, and may further enabling consistency and accuracy in saturation band placement.

Figure 2A:
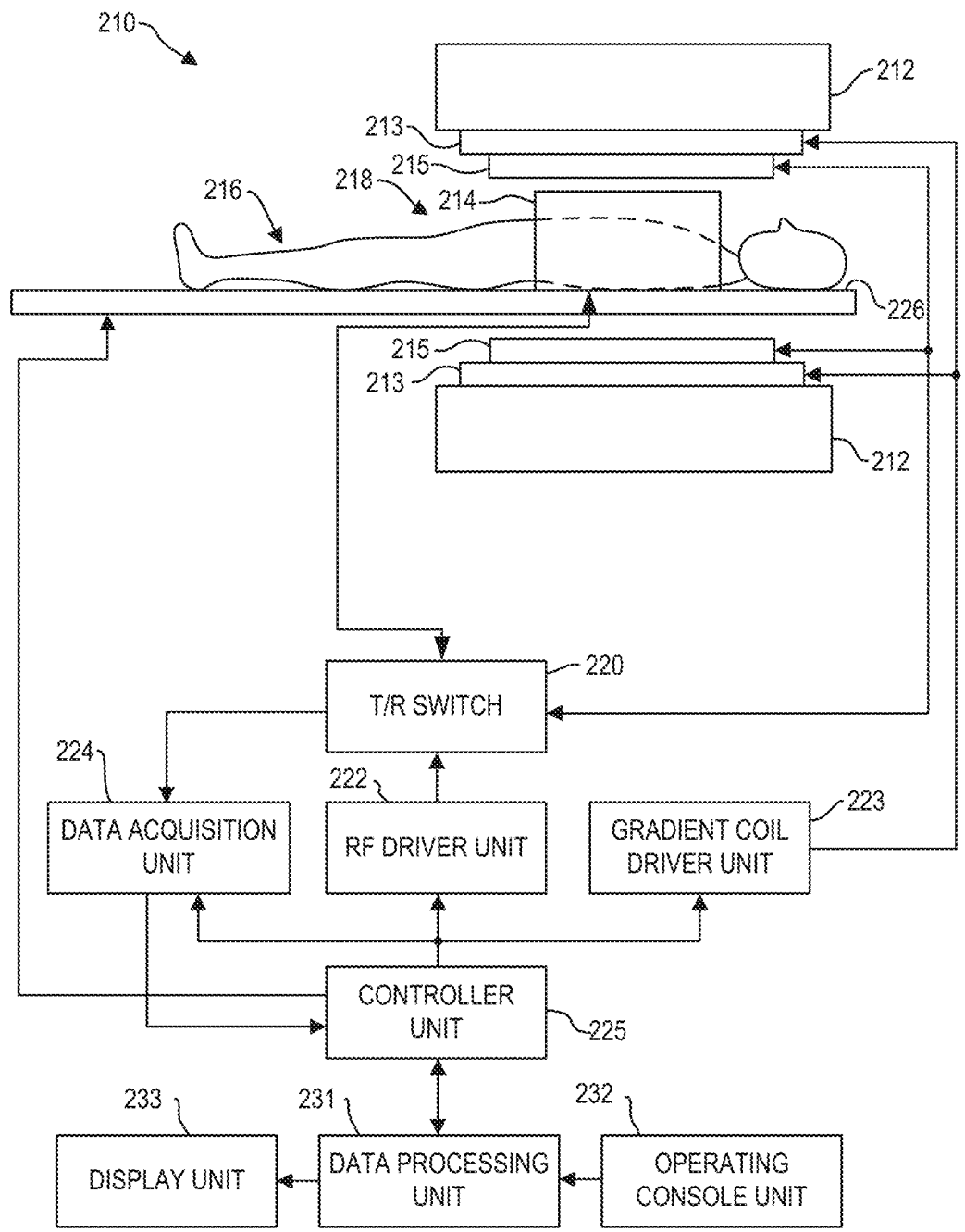
FIG. 2A is a MRI apparatus, according to an exemplary embodiment of the disclosure.
Figure 2B:
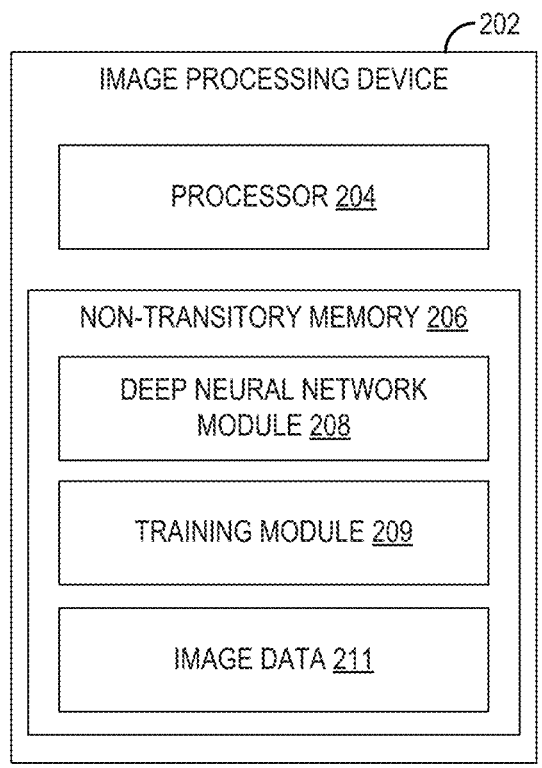
FIG. 2B is a block diagram of an image processing device which may be included in the MRI apparatus, according to an exemplary embodiment.
Figure 3:
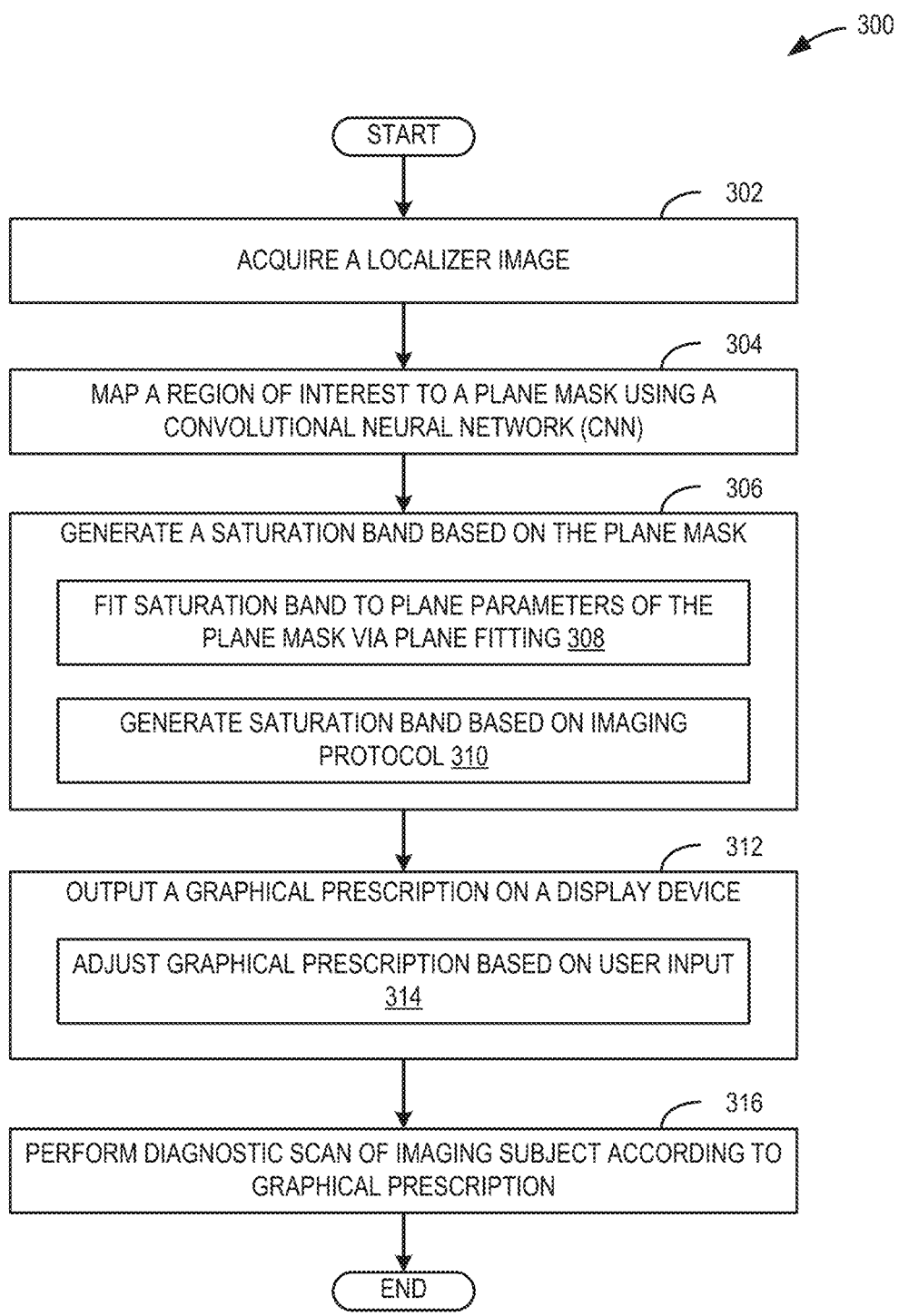
FIG. 3 is a flow chart illustrating a method for generating and prescribing at least one saturation band on a localizer image based on a plane mask, according to an exemplary embodiment.
Figure 4:
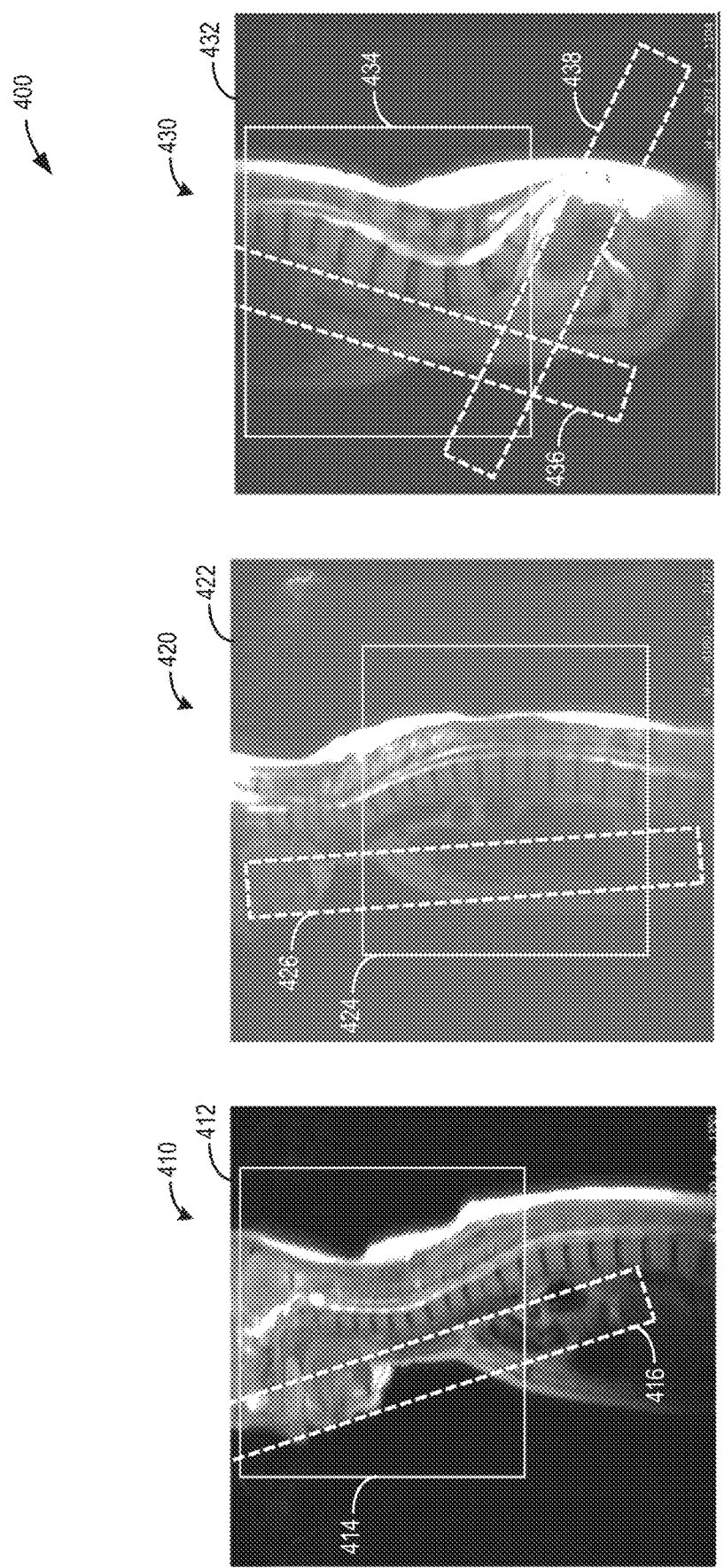
FIG. 4 shows a plurality of medical images, each having at least one saturation band overlaid thereon, according to an exemplary embodiment.

FIG. 1 illustrates a workflow for implementing a trained deep neural network to output at least one plane mask based on an input localizer image and to further automatically prescribe a corresponding number of saturation bands based on the at least one plane mask. FIG. 3 describes a method for automatically prescribing at least one saturation band and performing a MRI scan based on a graphical prescription, which includes the at least one saturation band. Examples of graphical prescriptions including at least one saturation band overlaid on a localizer image, which may be generated as described with respect to FIGS. 1, 3, are shown in FIG. 4. The deep neural network implemented as described with respect to FIGS. 1 and 3 may be trained using a plurality of training data pairs generated according to the methods described with respect to FIGS. 5-9, which may include generating training data based on curvature data, based on bounding boxes, and/or based on a trained regression model. The deep neural network may be trained using generated training data as described with respect to FIG. 10. The workflows and methods described herein may be implemented by an MRI apparatus, as shown in FIG. 2A, and an image processing device, as shown in FIG. 2B, which may be included in the MRI apparatus.

Turning to FIG. 1, an exemplary embodiment of a saturation band prediction workflow 100 is shown. Saturation band prediction workflow 100 is configured to acquire a localizer image of an imaging subject and identify at least one plane mask for the localizer image using a trained deep neural network. The plane mask may be a 3D projection which segments the localizer image as a binary plane mask, such that projecting the plane mask onto the localizer image provides lines on individual slides of localizer data, indicating a 3D plane of interest. Further, saturation band prediction workflow 100 may use a plane fitting method to generate a saturation band based on each of the at least one plane masks. At least one saturation band may be overlaid on the localizer image to give a graphical prescription, which may be displayed on a display device. Saturation band prediction workflow 100 may be implemented by an image processing system of an imaging device, such as a data processing unit 231 (of FIG. 2B) of a magnetic resonance imaging (MRI) apparatus 210 shown in FIG. 2A.

In the embodiment shown in FIG. 1, and as further described with respect to FIGS. 4, 7-9, the region of interest may be an anatomy (e.g., an anatomy of interest), such as an upper spine region, a mid-spine region, or a lower spine region. Although the saturation band prediction workflow 100 is herein described with respect to spine anatomy, the saturation band prediction workflow 100 may be applied to any anatomy or other imaging subject of interest for which suppression of a signal outside of the anatomy of interest using a saturation band is desired. Workflows and methods of FIGS. 3, 5-10 may be applied to localizer images and/or diagnostic medical images including anatomies or other imaging subjects of interest for which suppression of a signal outside of the anatomy of interest using a saturation band is desired, as further described herein.

Saturation band prediction workflow 100 may include a deep neural network configured to receive a localizer image 102 and segment the localizer image 102 to generate a plane mask based on the localizer image 102. The saturation band prediction workflow 100 may receive the localizer image 102 from a data acquisition unit 224 (of FIG. 2B) of the MRI apparatus 210 of FIG. 2A. The localizer image 102 may be a localizer image having a low resolution compared to a diagnostic medical image captured based on the graphical prescription, as further described herein with respect to FIG. 3. The localizer image 102 may be a 2D or a 3D localizer image and may be captured by the MRI apparatus 210 of FIG. 2A during a preliminary imaging scan. For example, the preliminary imaging scan may include performing an MRI scan without implementing saturation pulses. In some embodiments, the localizer image 102 comprises a matrix of intensity values in one or more color channels (e.g., a pixel-map), wherein each intensity value of each of the one or more color channels uniquely corresponds to an intensity value for an associated pixel. The localizer image 102 may include an image of an anatomical region of an imaging subject. In the example shown by FIG. 1, the localizer image 102 is an MRI image of a lower spine region of a patient.

The deep neural network may be a trained convolutional neural network (CNN) 104 comprised of one or more convolutional layers, wherein each of the one or more convolutional layers includes one or more filters, comprising a plurality of learnable weights, with a pre-determined receptive field and stride. For example, the deep neural network may comprise a plurality of convolutional filters, wherein a sensitivity of each of the plurality of convolutional filters is modulated by a corresponding spatial regularization factor. The trained CNN 104 is configured to map features of the localizer image 102 to a plane mask for at least a first anatomy of interest. Briefly, a localizer image (e.g., the localizer image 102) may be entered as input into the trained CNN 104, which may then output at least one plane mask based on the localizer image 102. In some embodiments, the trained CNN 104 may identify an anatomy of interest to which at least one plane mask may be mapped. In other embodiments, a desired anatomy of interest may be selected by a user, such as an MRI technologist, and the selected desired anatomy of interest may be input into the trained CNN 104. Details regarding training of the trained CNN 104 are described with respect to FIG. 10.

The at least one plane mask may be a binary mask which is generated by segmenting the localizer image 102 using the trained CNN 104, such that a plane identified by the plane mask is considered as a 3D projection (e.g., lines) on the localizer image 102. For example, a plane mask may be visualized as a line (e.g., a first plane mask 106, as described herein with respect to FIG. 1), where the line is a projection of a plane from a 3D coordinate system onto the coordinate system of the localizer image (e.g., the localizer image 102). Where the segmented plane is perpendicular to an image plane (e.g., the x-y plane, with respect to a reference axis system 130), the segmented plane may be visualized as a line (e.g., the first plane mask 106). The plane mask may have a variable width, as the segmented plane and the image plane may not perpendicularly intersect. Alternatively, the plane mask may indicate a line of perpendicular intersection between the segmented plane and the image plane. In some of a plurality of embodiments, the plane mask comprises a plurality or matrix of values, corresponding to the plurality of pixel intensity values of the localizer image 102, wherein each value of the plane mask indicates a classification of a corresponding pixel of the localizer image 102. In some embodiments, the plane mask may be a binary segmentation mask, comprising a matrix of 1's and 0's, wherein a 1 indicates a pixel belongs to an object class of interest, and a 0 indicates a pixel does not belong to the object class of interest. In some embodiments, the plane mask may comprise a multi-class segmentation mask, comprising a matrix of N distinct integers (e.g., 0, 1 . . . N), wherein each distinct integer corresponds uniquely to an object class, thus enabling the multi-class segmentation mask to encode position and area information for a plurality of object classes of interest. The values of the plane mask spatially correspond to the pixels and/or intensity values of the localizer image 102, such that if the plane mask was overlaid onto the localizer image 102, each value of the plane mask would align with (that is, be overlaid upon) a corresponding pixel of the localizer image 102, which an object classification for each pixel of the localizer image would be indicated by the corresponding value of the plane mask.

As shown in the saturation band prediction workflow 100, the localizer image 102 may be input into the trained CNN 104. The trained CNN 104 may identify at least one plane mask based on the localizer image 102. For example, as shown in FIG. 1, the trained CNN 104 may identify a first plane mask 106 and a second plane mask 108 for the localizer image 102, which includes a sacral spine curvature and a lumbar spine curvature in the spine anatomy of interest. As further described with respect to FIGS. 4, 7-9, for some anatomies, it may be desirable to identify a single plane mask which may be used to generate a single saturation band. For other anatomies, as described with respect to FIG. 1, such as a lower spine region, it may be desirable to identify more than one plane mask which may be used to generate a corresponding number of saturation bands. In this way, a signal from anatomies outside the anatomy of interest for regions having curved anatomies may be sufficiently suppressed by more than one saturation band, where each of the saturation bands are generated based on a respective plane mask.

In some of a plurality of embodiments, the at least one plane mask overlaid on the localizer image 102 may be displayed on a display device, such as a display device of the MRI apparatus 210 of FIG. 2A. Alternatively, the at least one plane mask overlaid on the localizer image 102 may not be displayed, and the first plane mask 106 and the second plane mask 108 overlaid on the localizer image 102 is shown in FIG. 1 for illustrative purposes.

A saturation band used to suppress signals from a region outside of the anatomy of interest may be generated based on the plane mask identified by the trained CNN 104. As described with respect to plane masks, when more than one plane mask is generated, a corresponding number of saturation bands may be generated, wherein a saturation band is generated based on each plane mask. For example, as shown in FIG. 1, a first saturation band 116 and a second saturation band 118 are generated based on the first plane mask 106 and the second plane mask 108. In the embodiment of FIG. 1, the first saturation band 116 and the second saturation band 118 are represented as boxes. This may be interpreted as areas covered by each of the first saturation band 116 and the second saturation band 118 are regions adjacent to the anatomy of interest and regions where a saturation pulse may be applied during a diagnostic scan. Further detail regarding saturation pulses and saturation band placement are described with respect to FIGS. 3-4.

The saturation band may be generated based on the respective plane mask using a plane fitting method 110. The plane mask identifies a 3D plane of the localizer image and the saturation band is a 2D band (e.g., single plane) overlaid on the localizer image, therefore the plane fitting method 110 may include identifying a position and an angulation of the plane mask and positioning the saturation band on the localizer image at the position and the angulation of the plane mask. In some embodiments, the plane fitting method 110 is performed as linear regression, using the following equation to fit the plane mask (e.g., where the plane mask may include a cloud of points in 3D space):

$$ax+by+cz+d=0$$

Parameters of the equation represent the normal vector and distance to origin for the given fitted plane (e.g., the saturation band being fit to the plane mask). Parameters of the equation may be adjusted such that the plane of interest passes as close as possible to as many segmented points of interest (e.g., the origin) as possible. This may minimize a metric, such as a sum of squared errors, to align the plane adjacent to the anatomy of interest.

Using the trained CNN 104 to identify the at least one plane mask and parameters (e.g., position and angulation) of the at least one plane mask, then generating at least one saturation band based on the at least one plane mask may allow for consistency in saturation band placement irrespective of changes in a position of the imaging subject. For example, when the imaging subject is a patient, the patient may shift positions, change poses, or otherwise move during imaging data collection (e.g., between the preliminary imaging scan and the imaging scan in which saturation pulses may be used). By identifying at least one 3D plane using the at least one plane mask and using the at least one 3D plane to generate at least one saturation band, placement of the at least one saturation band may be consistent with placement of the plane mask and thus consistent imaging data may be generated over multiple scans.

A width of each of the at least one saturation bands may be determined in response to input received from a user input device (e.g., the operating console unit 232). Alternatively, the width may be a pre-determined value stored in non-transitory memory as part of an imaging protocol, which may direct MR pulses over the imaging region and saturation pulses over regions indicated by the saturation band, as further described herein. The width, the position, and the angulation derived from the plane mask may be used to generate at least one saturation band, which may be overlaid on the localizer image 102 to give a graphical prescription 112. As further described with respect to FIG. 3, a method for saturation band prediction may further include adjustment of a band position and/or a band angulation of the at least one saturation band by the user, such as a MRI technologist. Following generation of the graphical prescription 112 and optional adjustment of the saturation band by the user, a diagnostic scan may be performed by the MRI apparatus 210 of FIG. 2A according to the graphical prescription 112, wherein the diagnostic scan may include performing one or more saturation pulses at a location dictated by the at least one saturation band. In this way, at least one saturation band may be automatically positioned on the localizer image 102 to direct a diagnostic scan, such that placement of saturation bands relative to the anatomy of interest is consistent (e.g., with respect to placement of the respective plane mask) and the diagnostic scan generates consistent imaging data irrespective of patient pose changes.

Referring to FIG. 2A, an MRI apparatus 210 is shown, in accordance with an exemplary embodiment. The MRI apparatus 210 may be the imaging device on which the saturation band prediction workflow 100 is implemented. Further methods and workflows described herein with respect to FIGS. 3-10 may also be implemented by the MRI apparatus 210, as further described with respect to FIG. 2B.

The MRI apparatus 210 includes a magnetostatic field magnet unit 212, a gradient coil unit 213, a RF coil unit 214, a RF body coil unit 215, a transmit/receive (T/R) switch 220, an RF driver unit 222, a gradient coil driver unit 223, a data acquisition unit 224, a controller unit 225, a patient table 226, a data processing unit 231, an operating console unit 232, and a display unit 233. In some embodiments, the RF coil unit 214 is a surface coil, which is a local coil typically placed proximate to the anatomy of interest of a subject 216. Herein, the RF body coil unit 215 is a transmit coil that transmits RF signals, and the RF coil unit 214 receives the MR signals. As such, the transmit body coil (e.g., RF body coil unit 215) and the surface receive coil (e.g., RF coil unit 214) are separate but electromagnetically coupled components. The MRI apparatus 210 transmits electromagnetic pulse signals to the subject 216 placed in an imaging space 218 with a static magnetic field formed to perform a scan for obtaining magnetic resonance signals from the subject 216. One or more images of the subject 216 can be reconstructed based on the magnetic resonance signals thus obtained by the scan. The magnetostatic field magnet unit 212 includes, for example, an annular superconducting magnet, which is mounted within a toroidal vacuum vessel. The magnet defines a cylindrical space surrounding the subject 216 and generates a constant primary magnetostatic field $B_0$.

The MRI apparatus 210 also includes a gradient coil unit 213 that forms a gradient magnetic field in the imaging space 218 so as to provide the magnetic resonance signals received by the RF coil arrays with three-dimensional positional information. The gradient coil unit 213 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 213 applies a gradient field in the slice selection direction (or scan direction) of the subject 216, to select the slice; and the RF body coil unit 215 or the local RF coil arrays may transmit an RF pulse to a selected slice of the subject 216. The gradient coil unit 213 also applies a gradient field in the phase encoding direction of the subject 216 to phase encode the magnetic resonance signals from the slice excited by the RF pulse. The gradient coil unit 213 then applies a gradient field in the frequency encoding direction of the subject 216 to frequency encode the magnetic resonance signals from the slice excited by the RF pulse.

The RF coil unit 214 is disposed, for example, to enclose the region to be imaged of the subject 216. In some examples, the RF coil unit 214 may be referred to as the surface coil or the receive coil. In the static magnetic field space or imaging space 218 where a static magnetic field $B_0$ is formed by the magnetostatic field magnet unit 212, the RF body coil unit 215 transmits, based on a control signal from the controller unit 225, an RF pulse that is an electromagnet wave to the subject 216 and thereby generates a high-frequency magnetic field B1. This excites a spin of protons in the slice to be imaged of the subject 216. The RF coil unit 214 receives, as a magnetic resonance signal, the electromagnetic wave generated when the proton spin thus excited in the slice to be imaged of the subject 216 returns into alignment with the initial magnetization vector. In some embodiments, the RF coil unit 214 may transmit the RF pulse and receive the MR signal. In other embodiments, the RF coil unit 214 may only be used for receiving the MR signals, but not transmitting the RF pulse.

The RF body coil unit 215 is disposed, for example, to enclose the imaging space 218, and produces RF magnetic field pulses orthogonal to the main magnetic field $B_0$ produced by the magnetostatic field magnet unit 212 within the imaging space 218 to excite the nuclei. In contrast to the RF coil unit 214, which may be disconnected from the MRI apparatus 210 and replaced with another RF coil unit, the RF body coil unit 215 is fixedly attached and connected to the MRI apparatus 210. Furthermore, whereas local coils such as the RF coil unit 214 can transmit to or receive signals from only a localized region of the subject 216, the RF body coil unit 215 generally has a larger coverage area. The RF body coil unit 215 may be used to transmit or receive signals to the whole body of the subject 216, for example. Using receive-only local coils and transmit body coils provides a uniform RF excitation and good image uniformity at the expense of high RF power deposited in the subject. For a transmit-receive local coil, the local coil provides the RF excitation to the anatomy of interest and receives the MR signal, thereby decreasing the RF power deposited in the subject. It should be appreciated that the particular use of the RF coil unit 214 and/or the RF body coil unit 215 depends on the imaging application.

The T/R switch 220 can selectively electrically connect the RF body coil unit 215 to the data acquisition unit 224 when operating in receive mode, and to the RF driver unit 222 when operating in transmit mode. Similarly, the T/R switch 220 can selectively electrically connect the RF coil unit 214 to the data acquisition unit 224 when the RF coil unit 214 operates in receive mode, and to the RF driver unit 222 when operating in transmit mode. When the RF coil unit 214 and the RF body coil unit 215 are both used in a single scan, for example if the RF coil unit 214 is configured to receive MR signals and the RF body coil unit 215 is configured to transmit RF signals, then the T/R switch 220 may direct control signals from the RF driver unit 222 to the RF body coil unit 215 while directing received MR signals from the RF coil unit 214 to the data acquisition unit 224. The coils of the RF body coil unit 215 may be configured to operate in a transmit-only mode or a transmit-receive mode. The coils of the RF coil unit 214 may be configured to operate in a transmit-receive mode or a receive-only mode.

The RF driver unit 222 includes a gate modulator (not shown), an RF power amplifier (not shown), and an RF oscillator (not shown) that are used to drive the RF coils (e.g., RF body coil unit 215) and form a high-frequency magnetic field in the imaging space 218. The RF driver unit 222 modulates, based on a control signal from the controller unit 225 and using the gate modulator, the RF signal received from the RF oscillator into a signal of predetermined timing having a predetermined envelope. The RF signal modulated by the gate modulator is amplified by the RF power amplifier and then output to the RF body coil unit 215.

The gradient coil driver unit 223 drives the gradient coil unit 213 based on a control signal from the controller unit 225 and thereby generates a gradient magnetic field in the imaging space 218. The gradient coil driver unit 223 includes three systems of driver circuits (not shown) corresponding to the three gradient coil systems included in the gradient coil unit 213.

The data acquisition unit 224 includes a pre-amplifier (not shown), a phase detector (not shown), and an analog/digital converter (not shown) used to acquire the magnetic resonance signals received by the RF coil unit 214. In the data acquisition unit 224, the phase detector phase detects, using the output from the RF oscillator of the RF driver unit 222 as a reference signal, the magnetic resonance signals received from the RF coil unit 214 and amplified by the pre-amplifier, and outputs the phase-detected analog magnetic resonance signals to the analog/digital converter for conversion into digital signals. The digital signals thus obtained are output to the data processing unit 231.

The MRI apparatus 210 includes a table 226 for placing the subject 216 thereon. The subject 216 may be moved inside and outside the imaging space 218 by moving the table 226 based on control signals from the controller unit 225.

The controller unit 225 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 225 is connected to the operating console unit 232 and processes the operation signals input to the operating console unit 232 and furthermore controls the table 226, RF driver unit 222, gradient coil driver unit 223, and data acquisition unit 224 by outputting control signals to them. The controller unit 225 also controls, to obtain a desired image, the data processing unit 231 and the display unit 233 based on operation signals received from the operating console unit 232.

The operating console unit 232 includes user input devices such as a touchscreen, keyboard and a mouse. The operating console unit 232 is used by an operator, for example, to input such data as an imaging protocol and to set a region where an imaging sequence is to be executed. The data about the imaging protocol and the imaging sequence execution region are output to the controller unit 225.

The display unit 233 includes a display device and displays an image on the display screen of the display device based on control signals received from the controller unit 225. The display unit 233 displays, for example, an image regarding an input item about which the operator inputs operation data from the operating console unit 232. The display unit 233 also displays a two-dimensional (2D) slice image or three-dimensional (3D) image of the subject 216 generated by the data processing unit 231. For example, the graphical prescription 112 of FIG. 1 may be displayed on the display unit 233, with the at least one saturation band overlaid on the localizer image 102. Additionally, a diagnostic medical image generated by a diagnostic MRI scan based on the graphical prescription 112 may be displayed on the display unit 233, as further described with respect to FIG. 3.

The data processing unit 231 includes a computer and a recording medium on which a program to be executed by the computer to perform predetermined data processing is recorded. The data processing unit 231 is connected to the controller unit 225 and performs data processing based on control signals received from the controller unit 225. The data processing unit 231 is also connected to the data acquisition unit 224 and generates spectrum data by applying various image processing operations to the magnetic resonance signals output from the data acquisition unit 224.

Turning to FIG. 2B, an image processing device 202 is shown, which may be implemented as or as an element of the data processing unit 231 of the MRI apparatus 210 of FIG. 2A. In some embodiments, at least a portion of the image processing device 202 is disposed at a remote device (e.g., edge device, server, etc.) communicably coupled to the MRI apparatus 210 via wired and/or wireless connections. In some embodiments, at least a portion of the image processing device 202 is disposed at a separate device (e.g., a workstation) which can receive images from the MRI apparatus 210 or from a storage device which stores the images generated by one or more additional imaging systems (e.g., MRI apparatuses). The image processing device 202 includes a processor 204 and a non-transitory memory 206, and is communicatively coupled to the operating console unit 232, the controller unit 225, and the display unit 233 of the MRI apparatus 210 of FIG. 2A.

The processor 204 is configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store deep neural network module 208, training module 209, and image data 211. For example, each of the deep neural network module 208 and the training module 209 may include code stored in the non-transitory memory 206 which may be executed by the processor 204 to implement the deep neural network and generate training data and/or train an untrained deep neural network, respectively. The deep neural network (e.g., code of the deep neural network module 208) may be implemented at the data processing unit 231 of the MRI apparatus 210. Generation of training data and/or training of an untrained deep neural network may be implemented at the data processing unit 231 of the MRI apparatus 210, on a remote server or computer coupled to the MRI apparatus 210, and so on.

Deep neural network module 208 may include one or more deep neural networks, comprising a plurality of weights and biases, activation functions, and instructions for implementing the one or more deep neural networks to receive localizer images and map the localizer images to a segmentation mask. For example, deep neural network module 208 may store instructions for implementing a CNN, such as the CNN of the saturation band prediction workflow 100. Deep neural network module 208 may include trained and/or untrained neural networks and may further include various metadata for the one or more trained or untrained deep neural networks stored therein. For example, the deep neural network module 208 may include a trained CNN, such as the trained CNN 104 of FIG. 1, and/or an untrained CNN, as further described with respect to FIGS. 5, 10.

Non-transitory memory 206 may further include training module 209, which comprises instructions for training one or more of the deep neural networks stored in deep neural network module 208. Training module 209 may include instructions that, when executed by processor 204, cause image processing device 202 to conduct one or more of the steps of method 1000, discussed in more detail below with reference to FIG. 10. In one example, training module 209 includes instructions for receiving training data pairs from image data 211, wherein said training data pair comprises a medical image and corresponding ground truth plane mask and/or plane parameters for use in training one or more of the deep neural networks stored in deep neural network module 208. In another example, training module 209 may include instructions for generating training data by executing one or more of the operations of the training data generation workflow 500 of FIG. method 600 of FIG. 6, and methods described with respect to FIGS. 7-9, discussed in more detail below. In some embodiments, the training module 209 is not disposed at the MRI apparatus 210 of FIG. 2A, but is located remotely and communicatively coupled to the MRI apparatus 210.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Non-transitory memory 206 may further store image data 211. Image data 211 may include localizer images, such as 2D or 3D localizer images of anatomical regions of one or more imaging subjects. In some embodiments, the images stored in image data 211 may have been acquired by the MRI apparatus 210. In some embodiments, the images stored in image data 211 may have been acquired by remotely located imaging systems, communicatively coupled to the MRI apparatus 210. Images stored in image data 211 may include metadata pertaining to the images stored therein. In some embodiments, metadata for localizer images stored in image data 211 may indicate one or more of image acquisition parameters used to acquire an image, a conversion factor for converting pixel/voxel to physical size (e.g., converting a pixel or voxel to an area, length, or volume corresponding to an area length or volume represented by said pixel/voxel), a date of image acquisition, an anatomy of interest included in the image, and so on.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration. It should be understood that the MRI apparatus 210 shown in FIG. 2A and the image processing device 202 shown in FIG. 2B are for illustration, not for limitation. Another appropriate image processing system and/or MRI apparatus may include more, fewer, or different components.

It will be appreciated that distinct systems may be used during a training phase and an implementation phase of one or more of the deep neural networks described herein. In some embodiments, a first system may be used to train a deep neural network by executing one or more steps of a training method, such as method 1000 described below, and a second separate system may be used to implement the deep neural network to prescribe at least one saturation band for a localizer image, such as by executing one or more of the steps of method 300, described below. Further, in some embodiments, training data generation may be performed by a third system, distinct from the first system and the second system, by executing one or more steps of method 600 and/or methods described with respect to FIGS. 5, 7-9, described below. As such, the first system, the second system, and the third system, may each comprise distinct components. In some embodiments, the second system may not include a training module, such as training module 209, as deep neural networks stored on non-transitory memory of the second system may be pre-trained by the first system. In some embodiments, the first system may not include an imaging device, and may receive images acquired by external systems communicably coupled thereto. However, in some embodiments a single system may conduct one or more or each of training data generation, deep neural network training, and implementation of the trained deep neural networks, disclosed herein.

As described above, placement of a saturation band on a localizer image (e.g., a 2D or 3D localizer image) may suppress a signal from outside of an anatomy of interest by indicating a region to be targeted by a saturation pulse during diagnostic imaging (e.g., to generate a diagnostic medical image). Referring to FIG. 3, a flow chart of a method 300 for generating and prescribing at least one saturation band on a localizer image based on a plane mask is shown. In some embodiments, the method 300 may be implemented by an imaging system, such as the MRI apparatus 210 of FIG. 2A, which may include the image processing device 202 of FIG. 2B.

At operation 302, the imaging system acquires a localizer image of an anatomical region of an imaging subject. The localizer image may be a 2D or a 3D localizer (e.g., a single or multi-plane) image generated from a MRI scan, and may have a first resolution. The first resolution may be a low resolution, compared to a resolution of a diagnostic medical image. For example, the localizer image may be the localizer image 102 of FIG. 1. In some embodiments, at operation 302 the imaging system acquires the localizer image using an imaging device, such as the MRI apparatus 210. For example, a preliminary scan may be performed to acquire the localizer image, where the preliminary scan may include a different intensity of MR pulses, compared to a diagnostic scan. In other embodiments, the imaging system receives the localizer image from an external device communicatively coupled to the imaging system, such as an image repository. The localizer image received at operation 302 may comprise a plurality of intensity values in one or more color channels, corresponding to a plurality of pixels. The plurality of intensity values may be arranged in a definite order. In some embodiments, the plurality of intensity values of the localizer image may comprise a 2D or 3D array or matrix, wherein each intensity value of the plurality of intensity values in a particular color channel may be uniquely identified by a first index and a second index, such as by a row number and a column number. In embodiments where the localizer image includes a plurality of color channels, the color channel to which an intensity value corresponds may be further indicated by a third index. The image may comprise a grayscale image or color image.

At operation 304, the imaging system maps a region of interest to a plane mask using a convolutional neural network (CNN). For example, the region of interest may be an anatomy of interest, such as a spine region, a shoulder region, a pelvic region, and so on. The method 300 is described herein with respect to FIG. 1, where the anatomy of interest is a mid-spine region, however the method 300 may also be used to map other anatomies of interest to a plane mask. The localizer image acquired at operation 302 may be entered as input into the CNN, which is trained to output at least one plane mask based on the localizer image. A plane mask of the at least one plane mask may be positioned adjacent to the anatomy of interest, such that a saturation band placed at the same position and angulation as the plane mask may suppress a signal from the underlying region (e.g., adjacent to the anatomy of interest) during a diagnostic scan.

For example, a localizer image may include an anatomy of interest with an anterior-most point, a posterior-most point, an inferior-most point and a superior-most point, where each of an anterior, a posterior, an inferior, and a superior direction are coplanar (e.g., the y-x plane with respect to the reference axis system 130 of FIG. 1) and the anterior and posterior directions are coaxial (e.g., the x-axis with respect to the reference axis system 130) and the inferior and superior directions are coaxial (e.g., the y-axis with respect to the reference axis system 130). The anterior-most point of the anatomy of interest may be a point at which the anatomy of interest is positioned posterior to the anterior-most point, and a region on an anterior side of the anterior-most point of the anatomy of interest does not include the anatomy of interest. Positioning a plane mask adjacent to the anatomy of interest may include positioning the plane mask at the anterior-most point of the anatomy of interest, where the plane mask is a linear plane that bisects the localizer image, such that a region on an anterior side of the plane mask does not include the anatomy of interest and a region on a posterior side of the plane mask includes the anatomy of interest.

For anatomies of interest which include curved regions, such as described with respect to FIG. 1, a linear plane positioned at the anterior-most point of the anatomy of interest may include anatomies other than the anatomy of interest in the region on the posterior side of the linear plane. Thus, an additional linear plane (e.g., plane mask) may be desired to exclude anatomies other than the anatomy of interest from the posterior side of the linear plane, such that signals from anatomies other than the anatomy of interest may be suppressed during diagnostic image capture. An anatomy of interest, such as a spine region including a lumbar spine curvature and a sacral spine curvature, as described with respect to FIG. 1, may have an inferior-most point in addition to the anterior-most point Similar to the anterior-most point, the inferior-most point of the anatomy of interest may be a point at which the anatomy of interest is positioned in a region superior to the inferior-most point. A region on the inferior side of the inferior-most point of the anatomy of interest does not include the anatomy of interest. Positioning a plane mask adjacent to the anatomy of interest may include positioning the plane mask at the inferior-most point of the anatomy of interest, where the plane mask is a linear plane that bisects the localizer image, such that a region on a superior side of the plane mask includes the anatomy of interest and a region on an inferior side of the plane mask does not include the anatomy of interest.

Saturation bands may be positioned at each of the planes positioned at the anterior-most point and the inferior-most point of the anatomy of interest. A width of the plane (e.g., along the x-axis, with respect to the reference axis system 130 of FIG. 1 for the second plane mask 108) may be any width extending in the anterior direction, relative to the anatomy of interest. A posterior side 134 of the second plane mask 108 may indicate the plane positioned at the anterior-most point of the anatomy of interest. As described with respect to FIG. 1 and further described herein, the second saturation band 118 may be positioned at the same position and angulation as the second plane mask 108. For example, a posterior-most side 144 of the second saturation band 118 may be positioned at the anterior-most point of the anatomy of interest. In other words, a position along the x-axis (with respect to the reference axis system 130) of the posterior side 134 of the second plane mask 108 may be equal to a position along the x-axis of the posterior-most side 144 of the second saturation band 118. For the sacral spine curvature, a superior side 154 of the first plane mask 106 may indicate the plane positioned at the inferior-most point of the anatomy of interest. The first saturation band 116 may be positioned at the same position an angulation as the first plane mask 106. For example, a superior-most side 164 of the first saturation band 116 may be positioned at the inferior-most point of the anatomy of interest. In other words, a position along the x- and y-axes (e.g., position and angulation, where angulation is an angle of the plane with respect to the y-axis) of the superior side 154 of the first plane mask 106 may be equal to a position along the x- and y-axes of the superior-most side 164 of the first saturation band 116. Placement of a saturation band (e.g., the first saturation band 116 and the second saturation band 118) may indicate a region for a saturation pulse during a diagnostic scan (as further described with respect to FIG. 3). Further examples of position and angulation of saturation bands based on a corresponding plane mask are described with respect to FIG. 4.

The CNN may be trained identify a number of plane masks, as well as a position and an angulation of the plane mask, based on anatomy included in the anatomy of interest. For example, as described above, different anatomies may have a different number of desired saturation bands as well as different positioning of the desired saturation bands, based on the anatomy. As described with respect to FIG. 1 and further described with respect to FIGS. 4, 5, 7, and 8, it may be desirable to identify two plane masks for a lower spine region including a sacral spine curve and a lumbar spine curve, thus allowing prescription of two corresponding saturation bands. In some embodiments, the CNN may be trained to identify anatomies within the anatomy of interest and determine a desired number of plane masks based on an anatomy of interest.

In other embodiments, a user may select an anatomy of interest to be scanned, where selection of the anatomy of interest includes selecting an anatomy of a plurality of anatomies listed on a user interface. For example, the plurality of anatomies may include an upper spine region, a mid-spine region, a lower spine region, a shoulder region, a pelvic region, and so on. The user may further select a time of flight angiography (TOF) scan. Based on the anatomy of interest and/or the scan selected by the user, the CNN may identify the anatomy of interest using feature mapping, in some embodiments.

In further embodiments, the user may position an imaging subject such that the anatomy of interest is positioned within a scan plane (e.g., within an area where the MRI apparatus may scan, such as the RF coil unit 214 of FIG. 2A). Upon initiation of the method 300, the MRI apparatus may scan the region present in the scan plane and at least one plane mask may be generated based on what the CNN is trained to identify as potential regions of interest.

The plane mask may be generated based on an underlying anatomy present in the localizer image. The CNN may identify at least one plane adjacent to the anatomy of interest and model the at least one plane as a 3D projection (e.g., a line projection, herein referred to as a plane mask) on the localizer image. The CNN may further segment the localizer image as a binary plane mask. In some embodiments, at least one plane mask may be overlaid on the localizer image and displayed on a display device. Alternatively, metadata of a position and an angulation of each of the at least one plane masks may be associated with a respective localizer image and may not be displayed on the display device.

At 306, the method 300 includes generating a saturation band based on the plane mask. When more than one plane mask is generated (e.g., output by the CNN based on the input localizer image), a saturation band may be generated based on each plane mask. Generating the saturation band may include, at operation 308, fitting the saturation band to plane parameters of the plane mask via plane fitting and, at operation 310, generating the saturation band based on an imaging protocol (e.g., based on a preset or user input width of the saturation band). Plane fitting may include identifying parameters of the plane mask, including a position and an angulation of the plane mask. For example, the position of the plane mask may include positioning along a horizontal axis of the localizer image, such as along an x-axis with respect to the reference axis system 130 of FIG. 1. A length of the plane mask may extend a length of the localizer image (e.g., along a y-axis with respect to the reference axis system 130) when the plane mask is vertical (e.g., parallel to the y-axis). The plane mask may also be positioned at an angle, where angulation of the plane mask may be in a y-x plane. When positioned at an angle, the length of the plane mask may extend a width of the localizer image (e.g., along the x-axis). The plane mask may have a predetermined width which is not equal to a width of the saturation band. A side of the plane mask (e.g., a superior side 132 of the first plane mask 106 or a posterior side 134 of the second plane mask 108 of FIG. 1) may be adjacent to the anatomy of interest and the predetermined width of the plane mask may extend in a direction opposite the side of the plane mask adjacent to the anatomy of interest. As described above, the plane mask may be a 3D projection displayed as a line. Therefore, the plane mask may indicate the position and angulation of a plane which extends into the localizer image (e.g., in a direction of a z-axis, with respect to the reference axis system 130), and the predetermined width of the plane mask may be irrelevant, as the side of the plane mask adjacent to the anatomy of interest identifies a plane of interest.

Plane parameters (e.g., position and angulation) may be identified by the CNN and output along with the plane mask as metadata of the localizer image, in some embodiments. In other embodiments, the plane mask may be output by the CNN as lines overlaid on the localizer image (e.g., as shown in FIG. 1) and plane parameters may be determined as an operation of plane fitting. Plane fitting may further include overlaying a saturation band on the localizer image at the position and angulation of the corresponding plane mask. The saturation band may be a 2D projection on the localizer image (e.g., a 2D or 3D localizer image) and may therefore not extend along the z-axis, counter to the plane mask. A length and a width of the saturation band may be equal to the length and the width of the plane mask, in some embodiments. In other embodiments, the length and the width of the saturation band may be predetermined based on the anatomy of the anatomy of interest, which may be determined by the CNN and/or preset by a user, as described above. The saturation band may have a predetermined width which may be adjusted by a user. For example, a user may input a desired width for a saturation band based on a selected anatomy to be imaged. Additionally or alternatively, the saturation band width may be preset (e.g., may be saved as part of an imaging protocol) and correspond to a selected anatomy of interest. Each saturation band of a plurality of saturation bands generated for a single localizer image may have the same width or may have different widths. In this way, at least one saturation band may be generated for a localizer image, where a number of saturation bands is equal to a number of plane masks output by the CNN.

At 312, the method 300 includes outputting a graphical prescription for display on a display device. The graphical prescription may include at least one saturation band overlaid on the localizer image used to map the at least one plane mask, where each saturation band of the at least one saturation band is generated based on a corresponding number of plane masks. The display device may be the display device of the display unit 233 of the MRI apparatus 210 of FIG. 2A. A user, such as a MRI technologist, may optionally adjust a band position and a band angulation of at least one saturation band of the graphical prescription. For example, the user may adjust the band position and/or band angulation of a saturation band which is at least partially overlapping the anatomy of interest so that signal from the anatomy of interest may not be suppressed during the diagnostic scan. At 314, the graphical prescription may be adjusted based on the user input (e.g., to adjust the band position and/or the band angulation). Adjustments to the graphical prescription based on the user input may be shown on the display device in real time or may be periodically updated to be shown on the display device.

At 316, the method 300 includes performing a diagnostic scan of the imaging subject according to the graphical prescription. The graphical prescription includes the localizer image which may have a first resolution which is lower than a desired resolution for analysis and diagnosis. Performing the diagnostic scan may include performing MR imaging, as described above, to acquire a diagnostic medical image of the same anatomy of interest as the localizer image with a higher resolution than the localizer image. Further, the diagnostic medical image may include suppressed signals from regions outside of the anatomy of interest (e.g., regions covered by the at least one saturation band). The diagnostic medical image may be acquired by applying conventional MR signals to the imaging subject in the imaging region (e.g., positioned in the RF coil unit 214 of FIG. 2A), and applying saturation pulses to regions dictated (e.g., outlined) by the at least one saturation band (e.g., as indicated by the graphical prescription). The saturation pulse may apply RF energy to suppress the MR signal from moving tissues outside of the imaged volume or to reduce and/or eliminate motion artifacts.

In some embodiments, acquisition of a localizer image (e.g., operation 302 of method 300) may be performed based on user input as described herein. Briefly, a user may select a desired anatomy of interest to be imaged from a list of anatomies provided on a display unit 233 using a user input device (e.g., the operating console unit 232 of FIG. 2A). Alternatively, an anatomy of interest may be automatically identified based on anatomical landmarks in the imaging region, and a localizer image may be captured which includes the automatically identified anatomy of interest. Mapping the region of interest (e.g., the anatomy of interest) to the plane mask is performed automatically by the CNN, and generation of the saturation band based on the plane mask is performed automatically by the processor using plane fitting. The generated plane mask is output for display on the display device, and user input may be used to adjust at least one of a position, an angulation, or a width of the saturation band. The user may provide input to the control unit via the operating console unit 232 that the position, angulation, and width of the saturation band are sufficient, and the diagnostic scan may be automatically performed, where the processor automatically identifies regions indicated by the at least one saturation band where a saturation pulse is desired. A diagnostic image generated by the diagnostic scan may be output for display on the display device and/or may be stored in the non-transitory memory 206 of the image processing device 202.

Patient motion may occur between capturing of the localizer image (e.g., the localizer image from which at least one plane mask is generated) and the diagnostic scan to capture the diagnostic medical image. Still, the saturation band may sufficiently cover regions outside of the anatomy of interest, and therefore suppress signal from tissues outside the anatomy of interest. Because the plane mask is a 3D projection into anatomy of the imaging subject, a 2D saturation band having a band position and a band angulation equal to that of the plane mask may allow for consistent imaging data to be generated regardless of patient motion.

Turning to FIG. 4, a plurality of graphical prescriptions 400 is shown, wherein each graphical prescription of the plurality of graphical prescriptions 400 includes at least one saturation band overlaid on a localizer image. The at least one saturation band may be generated based on at least one plane map output by a CNN trained to output a plane mask based on a localizer image, such as described with respect to the method 300 of FIG. 3. The plurality of graphical prescriptions 400 may be examples of graphical prescriptions output for display on a display device, such as the display unit 233 of the MRI apparatus 210 of FIG. 2A. Each of the plurality of graphical prescriptions 400 may thus be used to direct a diagnostic scan performed by a MRI apparatus, such as the MRI apparatus 210 of FIG. 2A.

A first graphical prescription 410 may include a first localizer image 412 with a third saturation band 416 overlaid thereon. As described with respect to the saturation band prediction workflow 100 of FIG. 1 and the method 300 of FIG. 3, a plane mask may be generated by the CNN based on an underlying anatomy of the first localizer image 412, and the third saturation band 416 may be generated based on the plane mask. In the first localizer image 412, an anatomy of interest includes an upper spine region of a patient. It may be determined by the CNN that, for an anatomy of interest (e.g., the upper spine region) of the first localizer image 412, a single saturation band may sufficiently block signals generated by anatomies outside of the anatomy of interest. The CNN may therefore generate a single plane mask in alignment with an anterior-most point of the anatomy of interest. The third saturation band 416 may be generated based on the plane mask, wherein a band position and a band angulation of the third saturation band 416 are equal to a position and an angulation of the plane mask. A width of the third saturation band 416 may be input by a user, such as an MRI technologist, as described with respect to method 300.

The first graphical prescription 410 further includes a first bounding box 414 overlaid on the first localizer image 412, where the first bounding box 414 indicates an imaging region. In some embodiments, the first bounding box 414 may not be input to the CNN when generating the plane mask. Instead, the first bounding box 414 may indicate a region to be imaged during a diagnostic scan by the MRI apparatus. In other embodiments, the first bounding box 414 may be placed by a user or automatically overlaid on the first localizer image 412 based on positioning of an imaging subject in a scan plane. When the first localizer image 412 including the first bounding box 414 is input into the CNN, the CNN may prescribe a plane mask based on an anatomy within the first bounding box 414.

As shown in the first graphical prescription 410, the third saturation band 416 may extend beyond the first bounding box 414. Inclusion of the first bounding box 414 in the first graphical prescription 410 may further assist a technologist in deciding whether to adjust the third saturation band 416, which has been automatically prescribed according to the saturation band prediction workflow 100 of FIG. 1 and the method 300 of FIG. 3. For example, the user may adjust at least one of the band position, the band angulation, and the width of the third saturation band 416. Following optional adjustment of the third saturation band 416, a diagnostic scan may be performed according to the first graphical prescription 410. In addition to a conventional MRI scanning procedure, the diagnostic scan may include implementing a saturation pulse in the region defined by the third saturation band 416. In this way, signals from tissues in the region of the third saturation band 416 may be blocked or suppressed, which may reduce signal interference and generate a diagnostic medical image wherein the anatomy of interest may be clearly distinguished from other anatomies. This may assist in patient diagnostics.

The plurality of graphical prescriptions 400 further includes a second graphical prescription 420, which may include a second localizer image 422 with a fourth saturation band 426 overlaid thereon. As described with respect to the saturation band prediction workflow 100 of FIG. 1 and the method 300 of FIG. 3, a plane mask may be generated by the CNN based on an underlying anatomy of the second localizer image 422, and the fourth saturation band 426 may be generated based on the plane mask. In the second localizer image 422, an anatomy of interest includes a mid-spine region of a patient. It may be determined by the CNN that, for an anatomy of interest (e.g., the mid-spine region) of the second localizer image 422, a single saturation band may sufficiently block signals generated by anatomies outside of the anatomy of interest. The CNN may therefore generate a single plane mask in alignment with an anterior most point of the anatomy of interest. The fourth saturation band 426 may be generated based on the plane mask, wherein a band position and a band angulation of the fourth saturation band 426 are equal to a position and an angulation of the plane mask. A width of the fourth saturation band 426 may be input by the user, as described with respect to method 300.

The second graphical prescription 420 further includes a second bounding box 424 overlaid on the second localizer image 422, where the second bounding box 424 indicates the imaging region. Similar to the first bounding box 414, the second bounding box 424 may not be input to the CNN when generating the plane mask. Instead, the second bounding box 424 may indicate a region to be imaged during a diagnostic scan by the MRI apparatus. In other embodiments, the second bounding box 424 may be placed by a user or automatically overlaid on the second localizer image 422 based on positioning of an imaging subject in a scan plane. When the second localizer image 422 including the second bounding box 424 is input into the CNN, the CNN may prescribe a plane mask based on an anatomy within the second bounding box 424.

As shown in the second graphical prescription 420, the fourth saturation band 426 may extend beyond the second bounding box 424. Inclusion of the second bounding box 424 in the second graphical prescription 420 may further assist a technologist in deciding whether to adjust the fourth saturation band 426, which has been automatically prescribed according to the saturation band prediction workflow 100 of FIG. 1 and the method 300 of FIG. 3. For example, the user may adjust at least one of the band position, the band angulation, and the width of the fourth saturation band 426. Following optional adjustment of the fourth saturation band 426, a diagnostic scan may be performed according to the second graphical prescription 420. In addition to a conventional MRI scanning procedure, the diagnostic scan may include implementing a saturation pulse in the region defined by the fourth saturation band 426. In this way, signals from tissues in the region of the fourth saturation band 426 may be blocked and/or suppressed, which may reduce signal interference and generate a diagnostic medical image wherein the anatomy of interest may be clearly distinguished from other anatomies. This may assist in patient diagnostics.

The plurality of graphical prescriptions 400 further includes a third graphical prescription 430, which may include a third localizer image 432 with a fifth saturation band 436 and a sixth saturation band 438 overlaid thereon. As described with respect to the saturation band prediction workflow 100 of FIG. 1 and the method 300 of FIG. 3, more than one plane mask may be generated by the CNN based on an underlying anatomy of the third localizer image 432, where the underlying anatomy has at least one curvature. For example, an anatomy of interest of the third localizer image 432 includes a lower spine region, comprising a lumbar spine curvature (e.g., a first curvature) and a sacral spine curvature (e.g., a second curvature). Each of the lumbar spine curvature and the sacral spine curvature may be approximately aligned along a different plane. For example, the lumbar spine curvature may be proximate to a vertical plane and the sacral spine curvature may be proximate to a horizontal plane. It may be determined by the CNN that more than one saturation band is desired to sufficiently block signals from anatomies outside of the anatomy of interest. The CNN may therefore generate a first plane mask to identify a plane adjacent to an anterior most point of the lumbar spine curvature and a second plane mask to identify a plane adjacent to an inferior most point of the sacral spine curvature. The fifth saturation band 436 and the sixth saturation band 438 may be generated based on the first plane mask and the second plane mask, respectively. A band position and a band angulation of the fifth saturation band 436 may be equal to a position and an angulation of the first plane mask, and a band position and a band angulation of the sixth saturation band 438 may be equal to a position and an angulation of the second plane mask. A width of each of the fifth saturation band 436 and the sixth saturation band 438 may be input by the user, and may be equal or different.

Inclusion of the fifth saturation band 436 and not the sixth saturation band 438 may allow signal from regions outside of the sacral spine curvature (e.g., inferior to the sacral spine curvature) to interfere with signal from both the lumbar spine curvature and signal from the sacral spine curvature. Inclusion of the sixth saturation band 438 and not the fifth saturation band 436 may allow signal from regions outside of the lumbar spine curvature (e.g., anterior to the lumbar spine curvature) to interfere with signal from both the lumbar spine curvature and signal from the sacral spine curvature. Therefore, it is desirable to include both the fifth saturation band 436 and the sixth saturation band 438, such that signal of the anatomy of interest is not interfered with by signal from tissues outside the anatomy of interest.

The third graphical prescription 430 further includes a third bounding box 434 overlaid on the third localizer image 432, where the third bounding box 434 indicates the imaging region. Similar to the first bounding box 414 and the second bounding box 424, the third bounding box 434 may not be input to the CNN when generating the first plane mask and the second plane mask. Instead, the third bounding box 434 may indicate a region to be imaged during a diagnostic scan by the MRI apparatus. In other embodiments, the third bounding box 434 may be placed by a user or automatically overlaid on the third localizer image 432 based on positioning of an imaging subject in a scan plane. When the third localizer image 432 including the third bounding box 434 is input into the CNN, the CNN may prescribe a plane mask based on an anatomy within the third bounding box 434.

As shown in the third graphical prescription 430, the fifth saturation band 436 and the sixth saturation band 438 may extend beyond the third bounding box 434. Inclusion of the third bounding box 434 in the third graphical prescription 430 may further assist a technologist in deciding whether to adjust either or both of the fifth saturation band 436 and the sixth saturation band 438, which have been automatically prescribed according to the saturation band prediction workflow 100 of FIG. 1 and the method 300 of FIG. 3. For example, the user may adjust at least one of the band position, the band angulation, and the width of either or both of the fifth saturation band 436 and the sixth saturation band 438. Following optional adjustment of either or both of the fifth saturation band 436 and the sixth saturation band 438, a diagnostic scan may be performed according to the third graphical prescription 430. In addition to a conventional MRI scanning procedure, the diagnostic scan may include implementing a saturation pulse in the region defined by the fifth saturation band 436 and the sixth saturation band 438. In this way, signals from tissues in the region of the fifth saturation band 436 and the sixth saturation band 438 may be blocked and/or suppressed, which may reduce signal interference and generate a diagnostic medical image wherein the anatomy of interest may be clearly distinguished from other anatomies. This may assist in patient diagnostics.

Described with relation to FIGS. 1-4 are systems, methods, and embodiments thereof for generating at least one saturation band based on at least one plane mask output by a CNN. A localizer image is input into the CNN, which is trained to output at least one plane mask based on a localizer image. Plane fitting is performed to position a saturation band at a position and an angulation of each of the at least one plane masks. A graphical prescription, which includes at least one saturation band overlaid on the localizer image, is output for display on a display device and may be used to perform a diagnostic scan. The diagnostic scan may include at least one saturation pulse at regions outlined by the at least one saturation band to block signals from tissues outside of the anatomy of interest. By first identifying a plane adjacent to the anatomy of interest, where the plane (e.g., which may be indicated by the plane mask) is a 3D projection extending into the localizer image, which may be a 2D or 3D image, the corresponding saturation band may sufficiently suppress signals outside of the anatomy of interest, regardless of potential imaging subject movement or pose changes between a preliminary imaging scan and a diagnostic scan.

Prior to implementation of the CNN, the CNN is trained to map an anatomy of interest to at least one plane mask based on the underlying anatomy of the localizer image. Training data used to train the CNN may be automatically generated, as is described with respect to a training data generation workflow of FIG. 5 and a method of generating training data of FIG. 6. Training data may be generated in more than one way, such as based on curvature data, as described with respect to FIG. 7, and/or based on bounding boxes, as described with respect to FIGS. 8-9. Generated training data may be input into an untrained CNN to train the untrained CNN to output at least one plane mask based on an anatomy of a localizer image. Training of the untrained CNN is described with respect to FIG. 10. A resulting trained CNN may be implemented in the saturation band prediction workflow 100 of FIG. 1 and the method 300 of FIG. 3, as described above.

Figure 5:
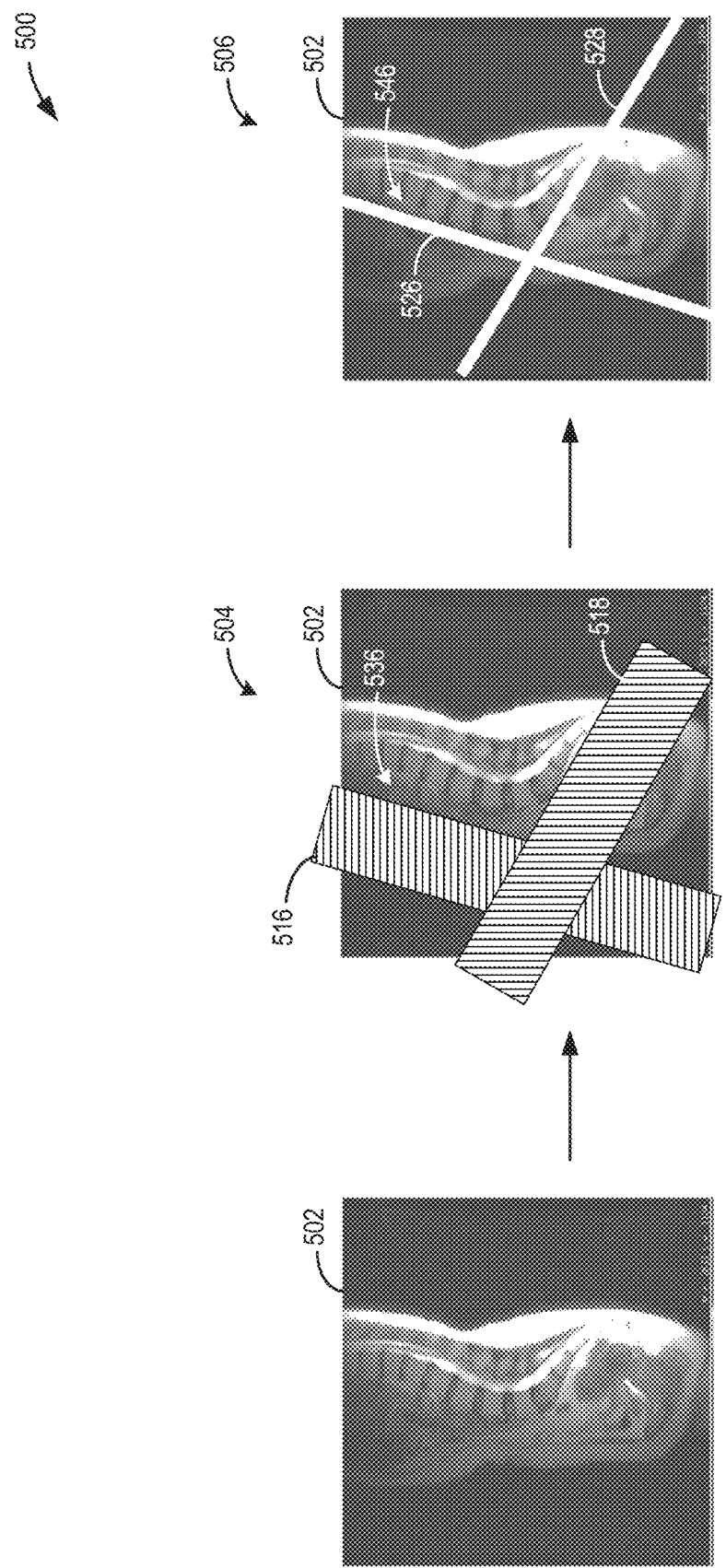
FIG. 5 is a workflow of a method for generating training data which may be used to train a deep neural network to output a plane mask based on a localizer image, according to an exemplary embodiment.

Turning to FIG. 5, an exemplary embodiment of a training data generation workflow 500 is shown. Briefly, the training data generation workflow 500 includes acquiring a medical image of an imaging subject, generating at least one saturation band based on the medical image, and identifying one or more plane parameters of the at least one saturation band by generating a plane projection based on the saturation band. The training data generation workflow 500 may be implemented by one or more of the systems disclosed herein, such as the MRI apparatus 210 of FIG. 2A and/or the image processing device 202 of FIG. 2B.

Training data generation workflow 500 is configured to generate training data pairs, which may include a medical image, such as a 2D or 3D localizer image captured during a diagnostic scan (e.g., a diagnostic medical image), and an associated ground truth. The associated ground truth may include a set of plane parameters (e.g., ground truth parameters) for a plane from which a desired saturation band may be generated, including a plane position and a plane angulation. Additionally or alternatively, the associated ground truth may be a graphical projection including a plane projection overlaid on the diagnostic medical image. Training data pairs generated by the training data generation workflow 500 may be employed in a training method, such as a method 1000 of FIG. 10, to train a deep neural network for generating and outputting at least one plane mask based on a localizer image, such as the trained CNN 104 of the saturation band prediction workflow 100 of FIG. 1 and the CNN of the method 300 of FIG. 3.

The training data generation workflow 500 may acquire a medical image, such as a diagnostic medical image 502, generated from a diagnostic MRI scan. The diagnostic medical image 502 may be a 2D or a 3D localizer image with a high resolution (e.g., compared to a localizer image which may be captured during a preliminary scan). In some embodiments, the imaging system acquires the diagnostic medical image 502 using an imaging device, such as the MRI apparatus 210. In other embodiments, the imaging system receives the diagnostic medical image 502 from an external device communicatively coupled to the imaging system, such as an image repository.

The training data generation workflow 500 may further include inputting the diagnostic medical image 502 into a segmentation method which may generate a segmentation mask of the diagnostic medical image 502 to identify a region of interest of the diagnostic medical image 502. The region of interest may include an anatomy of interest, such as an upper spine region, a mid-spine region, a shoulder, and so on. In the embodiment shown in FIG. 5, the diagnostic medical image 502 includes an anatomy of interest including a lower spine region comprised of a lumbar spine curvature (e.g., a first curvature) and a sacral spine curvature (e.g., a second curvature). Anatomical landmarks of the anatomy of interest which may be used for saturation band placement may be identified using the segmentation mask.

The training data generation workflow 500 further comprises generating a first graphical prescription 504, wherein the graphical prescription includes the diagnostic medical image 502 with at least one saturation band overlaid thereon. The at least one saturation band is a 2D projection on the diagnostic medical image 502, which may be a 2D or a 3D localizer image. In some embodiments, the at least one saturation band may be manually placed on the diagnostic medical image 502 by a user, such as an MRI technologist or other user trained to place saturation bands on diagnostic medical images. In other embodiments, the at least one saturation band may be automatically placed by a trained deep neural network. For example, the diagnostic medical image may be input into a deep neural network trained to output a graphical prescription (e.g., the first graphical prescription 504) including at least one saturation band overlaid on the diagnostic medical image.

In the embodiment shown in FIG. 5, a seventh saturation band 516 and an eighth saturation band 518 are overlaid on the diagnostic medical image 502. The seventh saturation band 516 is aligned along a length of the seventh saturation band 516 with an anterior most point of the lumbar spine curvature and the eighth saturation band 518 is aligned along a length of the eighth saturation band 518 with an inferior most point of the sacral spine curvature, such that a width of each of the at least one saturation bands extends away from the anatomy of interest. Both the seventh saturation band 516 and the eighth saturation band 518 are therefore positioned to block signals from tissues other than those in the lower spine region during a MRI scan.

In the training data generation workflow 500, a MRI scan may not be performed and instead the first graphical prescription 504, including the at least one saturation band, is converted to a second graphical prescription 506, which includes at least one plane projection to identify the one or more plane parameters. Conversion of the first graphical prescription 504 may include indicating a desired plane projection at a band position and a band angulation of each of the at least one saturation bands. The at least one plane projection may identify a 3D plane of the diagnostic medical image 502, which may be a 2D or a 3D localizer image captured by a diagnostic MRI scan. The second graphical prescription 506 thus includes the diagnostic medical image 502 with a number of plane projections overlaid thereon, where the number of plane projections is equal to a number of saturation bands overlaid on the first graphical prescription 504. In the embodiment of FIG. 5, a first plane projection 526 is overlaid on the diagnostic medical image 502 in place of the seventh saturation band 516 and a second plane projection 528 is overlaid on the diagnostic medical image 502 in place of the eighth saturation band 518. Converting each of the at least one saturation band to the at least one plane projection may include identifying one or more plane parameters of the saturation band and identifying a plane having equal parameters. For example, a band position and a band angulation of the eighth saturation band 518 is equal to a position and an angulation of the second plane projection 528.

Each of the seventh saturation band 516 and the eighth saturation band 518 have an associated width, which may be input by a user or may be a pre-set value. As previously stated, each of the at least one saturation band is a 2D projection overlaid on the diagnostic medical image 502, wherein each of the at least one saturation band has a length and a width. Each of the first plane projection 526 and the second plane projection 528 may be a 3D projection overlaid on the diagnostic medical image 502, wherein each of the at least one plane projection has a length and a width, as well as a depth which extends into a thickness of the diagnostic medical image 502 when the diagnostic medical image 502 is a 3D image. A position of each of the at least one plane projection may be based on a side of the respective saturation band adjacent to the anatomy of interest. For example, the first plane projection 526 may be positioned such that a posterior side 546 of the first plane projection 526 is at a position and an angulation of a posterior side 536 of the seventh saturation band 516.

In some embodiments, the training data pair may include the diagnostic medical image with at least one plane projection overlaid thereon (e.g., the second graphical prescription 506), as described with respect to FIG. 5. In other embodiments, the training data pair may include the diagnostic medical image with associated metadata indicating a position and an angulation of at least one plane projection identified according to the workflow described with respect to FIG. 5 and/or the method 600 of FIG. 6. As further described herein with respect to FIGS. 6-9, training data pair may be generated according to at least one of a plurality of methods, where plane parameters for at least one plane projection for a diagnostic medical image may be determined based on curvature data, based on at least one bounding box of the diagnostic medical image, and/or using a trained regression network.

Figure 6:
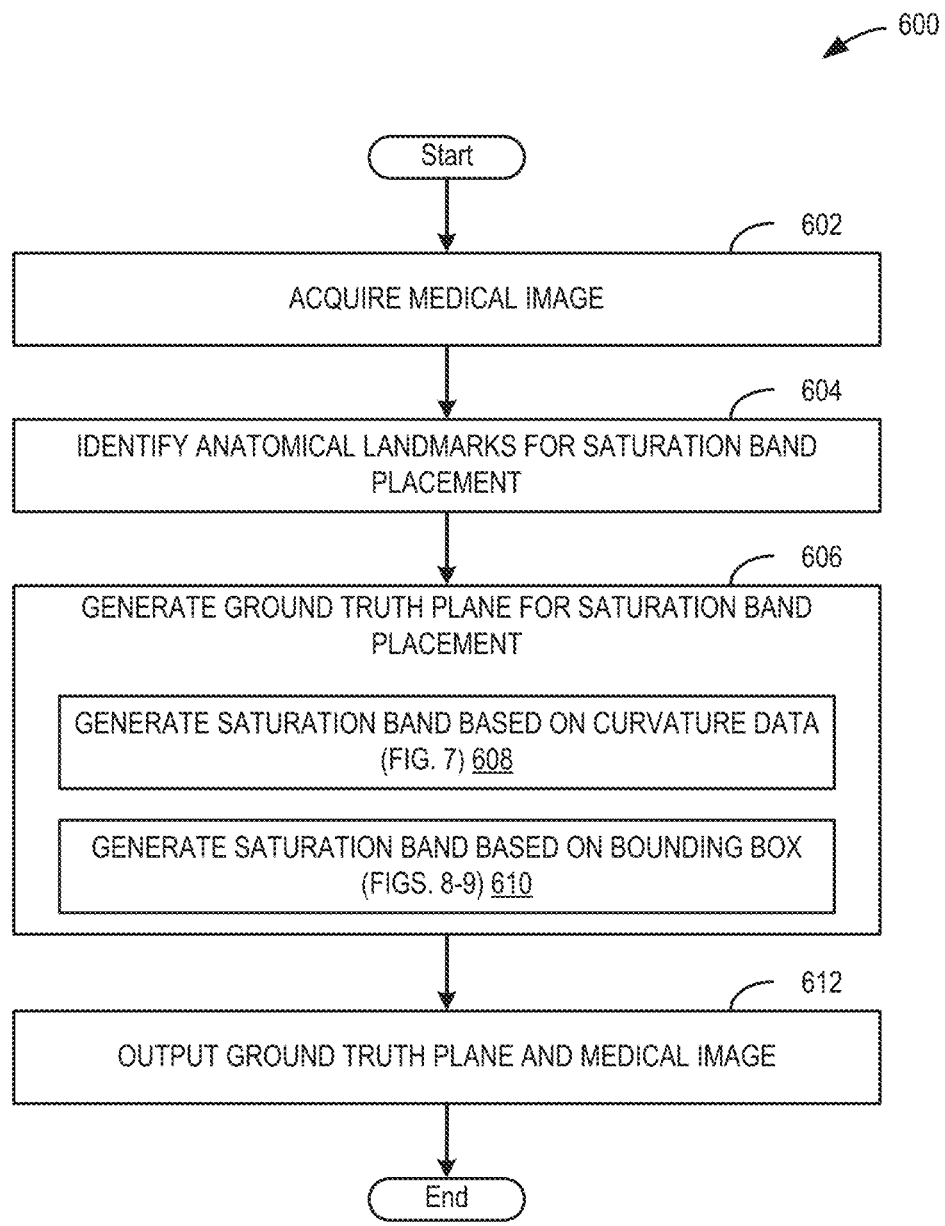
FIG. 6 is a flow chart illustrating a method for generating training data, according to an exemplary embodiment.

Turning now to FIG. 6, a method 600 for generating training data (e.g., a diagnostic medical image and one or more plane parameters therefore) is shown. As described with respect to the training data generation workflow 500, generating training data may include acquiring a diagnostic medical image of an imaging subject, generating a saturation band based on the diagnostic medical image, and identifying one or more plane parameters of the saturation band. As described herein with respect to FIG. 6, the saturation band may be generated using a plurality of methods, which may include fitting a bounding box to anatomical landmarks and/or using anatomy curvature information. The method 600 may be executed by one or more of the systems described herein, such as the MRI apparatus 210 of FIG. 2A, and/or the image processing device 202 of FIG. 2B. Method 600 may be executed as part of a workflow for generating training data, such as the training data generation workflow 500.

At 602, the method 600 includes acquiring a diagnostic medical image. The diagnostic medical image may be a high-resolution image compared to a localizer image which may be input to a CNN trained to output at least one mask from which a corresponding number of saturation bands may be generated, in accordance with FIGS. 1 and 3, and may be captured by a diagnostic MRI scan. In some embodiments, the imaging system implementing the method 600 receives the localizer from an external device communicatively coupled to the imaging system, such as an image repository. The diagnostic medical image acquired at operation 602 may comprise a plurality of intensity values in one or more color channels, corresponding to a plurality of pixels. The plurality of intensity values may be arranged in a definite order. In some embodiments, the plurality of intensity values of the diagnostic medical image may comprise a 2D or 3D array or matrix, wherein each intensity value of the plurality of intensity values in a particular color channel may be uniquely identified by a first index and a second index, such as by a row number and a column number. In embodiments where the diagnostic medical image includes a plurality of color channels, the color channel to which an intensity value corresponds may be further indicated by a third index. The diagnostic medical image may comprise a grayscale image or color image.

Figure 7:
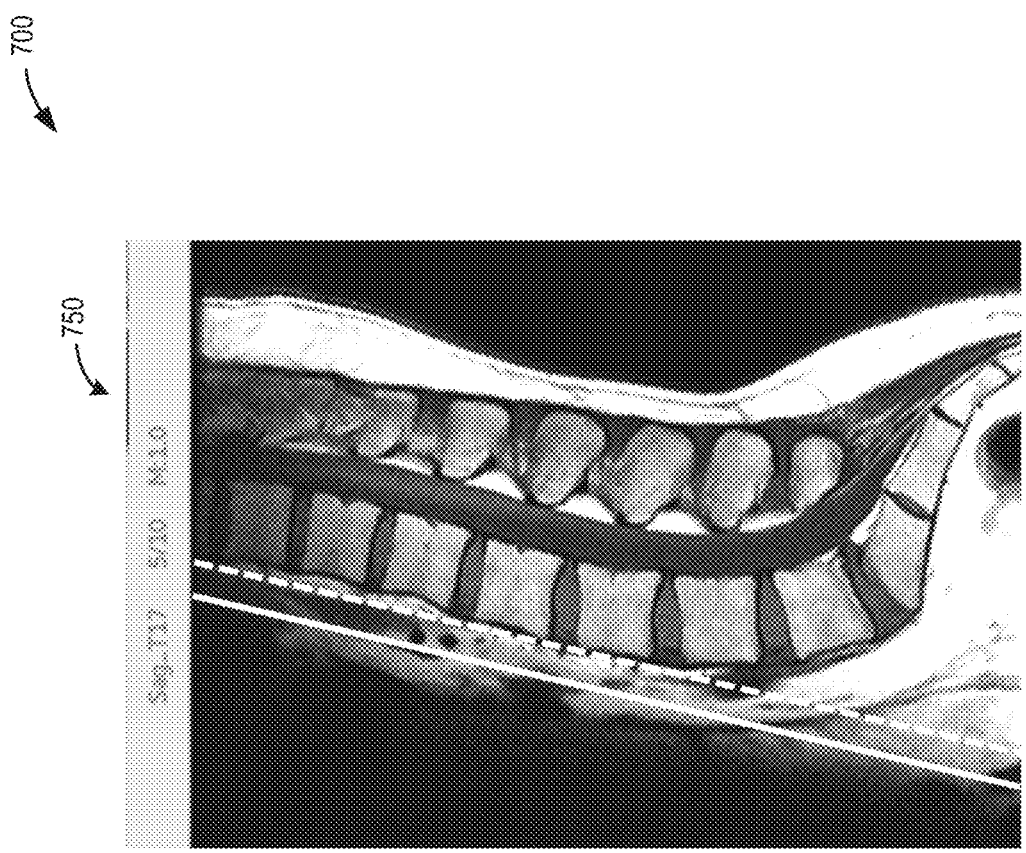
FIG. 7 shows a plurality of images used to generate training data based on curvature data, according to an exemplary embodiment.
Figure 7:
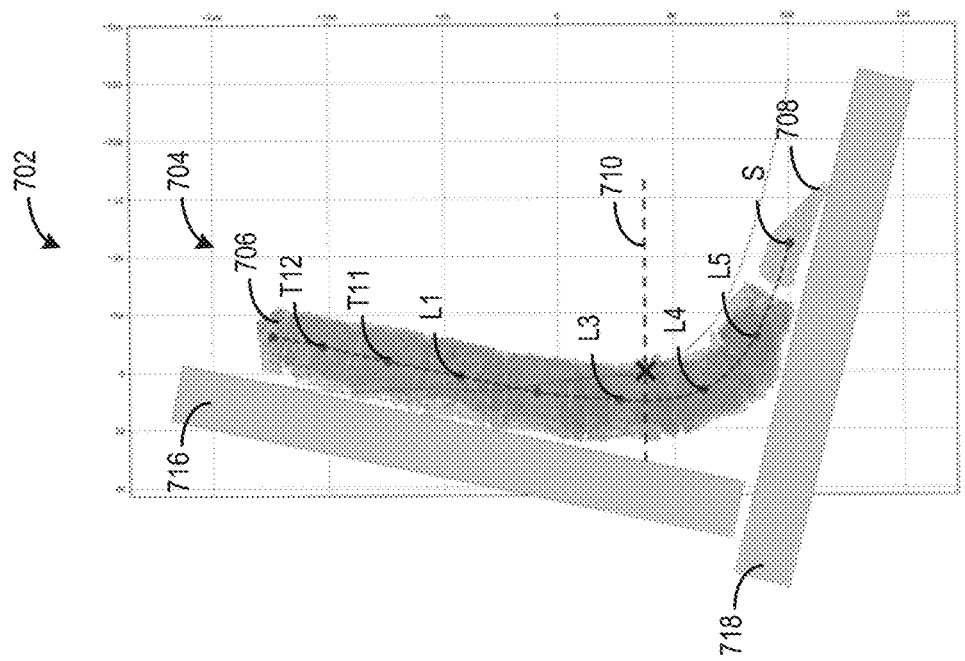
Figure 8:
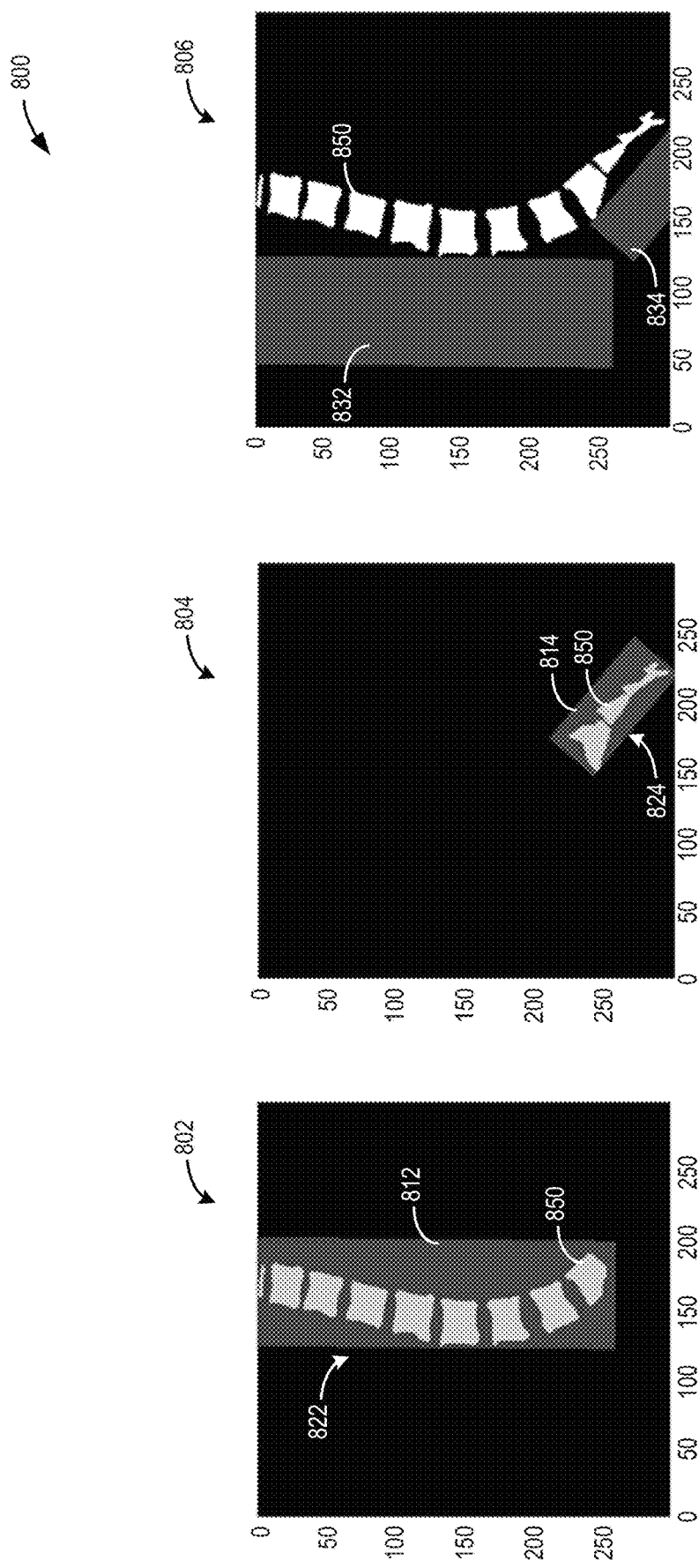
FIG. 8 shows a plurality of images of a first anatomy of interest used to generate training data based on bounding boxes, according to an exemplary embodiment.
Figure 9:
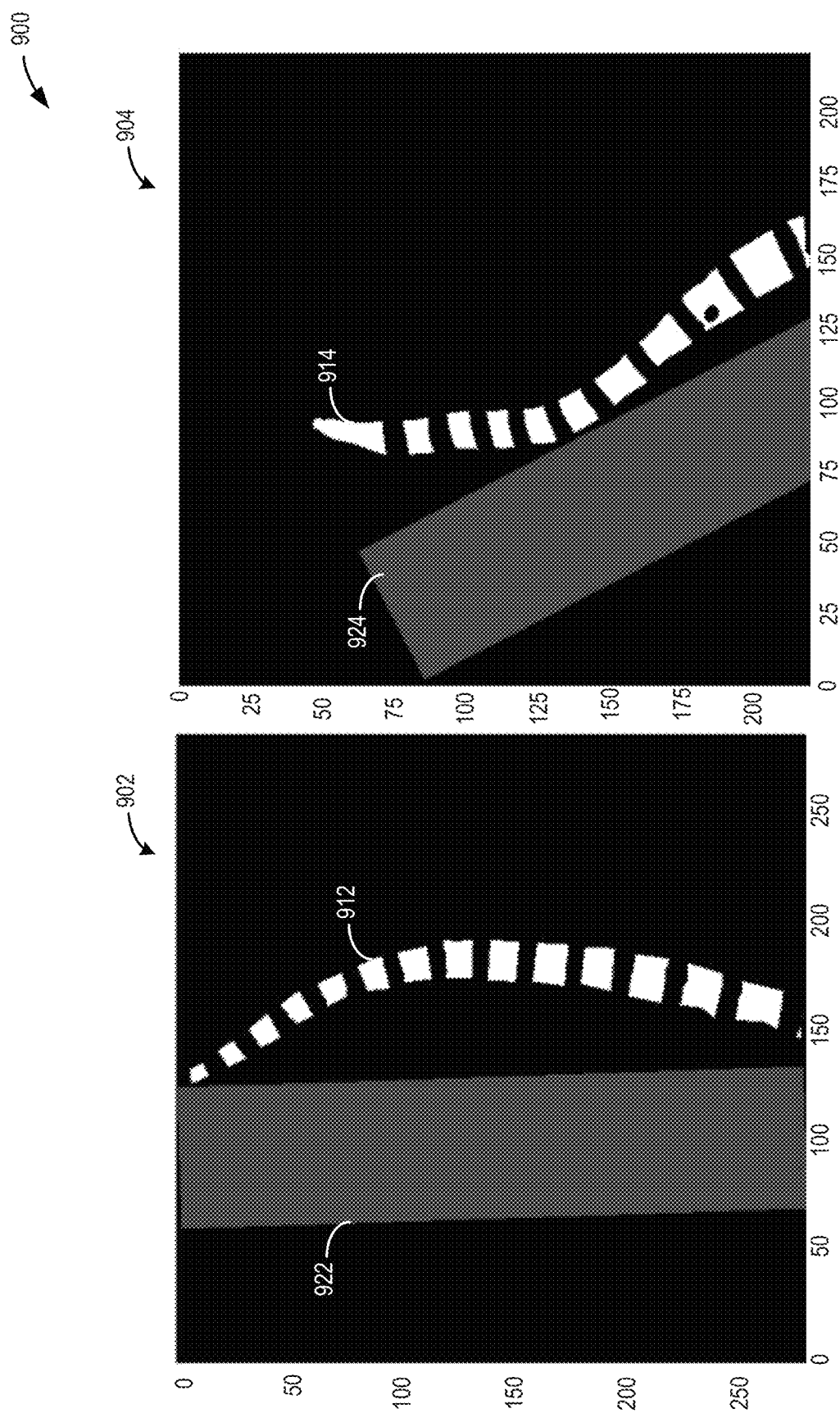
FIG. 9 shows a plurality of images of a second anatomy of interest used to generate training data based on bounding boxes, according to an exemplary embodiment.

At 604, the method 600 includes identifying anatomical landmarks for saturation band placement. For example, within a region of interest identified by a user or within an imaging region captured in the image, the method 600 may identify anatomies of interest and determine a corresponding anatomy. In the examples of FIGS. 5 and 7, identification of a sinusoidal curved spine region may indicate that the anatomy of interest is a lower spine region for which more than one saturation band may be desired. In the example of FIG. 9, a concave or convex curved spine region may indicate a mid- or upper spine region, for which a single saturation band may sufficiently block or suppress signals from outside the anatomy of interest. Generation of saturation bands for different anatomies is further described with respect to FIGS. 7-9.

In some embodiments, identifying anatomical landmarks for saturation band placement may be done by generating a segmentation mask of the diagnostic medical image to identify the anatomy of interest. In other embodiments, a deep learning neural network may be trained to identify anatomies of interest in a diagnostic medical image. The trained deep learning neural network may be implemented in the method 600 to identify anatomical landmarks. Other methods for identifying anatomical landmarks and, based on identified anatomical landmarks, identifying a number and approximate orientation of saturation bands, may include manual user identification and/or other machine learning-based methods.

At 606, the method 600 includes generating a ground-truth plane for saturation band placement. Identifying anatomical landmarks at the operation 604 may indicate a number and approximate placement of saturation bands for the diagnostic medical image and operation 606 may include positioning (e.g., adjusting approximate placement of) each of the at least one saturation bands on the diagnostic medical image. As described with respect to FIGS. 1 and 5, a side of a saturation band may be positioned adjacent to, but not overlapping, an anatomy of interest. For example, as described with respect to FIG. 5, the posterior side 536 of the seventh saturation band 516 may be adjacent to an anterior side of the lumbar spine curvature. At least one saturation band (e.g., where a number of saturation bands may correspond to an anatomy of interest) may be positioned by a user, using a trained deep neural network, or another method for positioning a saturation band relative to an anatomy of interest.

For example, at 608, the method 600 may include generating at least one saturation band based on curvature data of the anatomy of interest. Turning to FIG. 7, a plurality of images 700 demonstrating generation of training data based on curvature data are shown. As described with respect to FIG. 6, generating training data may include generating a segmentation mask of a diagnostic medical image to identify an anatomy of interest of the diagnostic medical image. In the embodiment shown in FIG. 7, the method 600 may identify the anatomy of interest as the lower spine region based on anatomical landmarks and infer that the anatomy captured by a diagnostic medical image 750 includes lumbar vertebrae and the sacrum.

A graphical prescription 702 of the diagnostic medical image 750 shows a segmentation mask 704 of a lower spine region, including a first curvature (e.g., a lumbar spine curvature) and a second curvature (e.g., a sacral spine curvature). The lumbar spine curvature may be represented as a first region 706 of the segmentation mask 704 and the sacral spine curvature may be represented as a second region 708 of the segmentation mask 704. A dashed line runs through a center of the segmentation mask 704 and indicates each vertebra of the lower spine region with a point. Together, the points and the dashed line indicate curvature of the lower spine region. The graphical prescription 702 further includes an anterior saturation band 716 and an inferior saturation band 718. Positioning of each of the anterior saturation band 716 and the inferior saturation band 718 may be determined based on curvature-based thresholds.

For example, the dashed line of the segmentation mask 704 may be approximately linear above a horizontal dashed line 710. As described with respect to operation 604 of FIG. 6, generating a saturation band based on curvature data may include positioning an anterior saturation band adjacent to an approximately linear region of the lower spine region. Additionally or alternatively, the anterior saturation band may be positioned based on anatomical landmarks (e.g., as identified at operation 604). For example, the anterior saturation band may be positioned parallel to the dashed line of the segmentation mask from a L1, T11, or T12 vertebrae to a L4 or L3 vertebrae, as indicated on the graphical prescription 702. A first curvature-based threshold may be used to select a superior vertebra to fit the anterior saturation band to (e.g., from among the L1, T11, or T12 vertebrae). For example, the first curvature-based threshold may be a percentage or angle of deviation from a linear line between a superior-most vertebra (e.g., T12) and other vertebrae in the lumbar spine curve (e.g., the T11, L1, L2, L3, L4, and L5 vertebrae). The superior vertebra used to fit the anterior saturation band may be selected as the most superior vertebra (e.g., of the L1, T12, and T11 vertebrae) which is in linear alignment with other vertebrae of the lumbar spine curve. For example, if the T12 vertebra deviates from linear alignment with other vertebra by at least 30 degrees, the T11 vertebra may be selected as the superior vertebra to fit the anterior saturation band. The first curvature-based threshold may be set and/or adjusted by a user, determined by a deep neural network, or any other sufficient methods. In the embodiment shown in FIG. 7, the anterior saturation band 716 may be positioned approximately parallel to the dashed line of the segmentation mask 704 between the T12 and the L3 vertebrae. In this way, the anterior saturation band (e.g., the anterior saturation band 716) is fit to anterior points of the segmentation mask 704 and the anterior saturation band is parallel to a plane defined by the linear portion of the dashed line of the segmentation mask 704. Offset of the anterior saturation band from an anterior-most point of the segmentation mask 704 may be pre-determined, for example, may be offset by a pre-determined distance input by a user or based on the anatomy identified in the graphical prescription 702.

For anatomies in which a second saturation band is desired, such as the low spine region, an inferior saturation band for the sacral spine curve may also be positioned based on curvature data. The inferior saturation band may be positioned based on an approximate alignment of an S1 vertebra and the rest of the sacrum (e.g., the second region 708). Similar to placement of the anterior saturation band, the inferior saturation band may be positioned parallel to a linear region of the dashed line of the segmentation mask 704 in the second region 708. The inferior saturation band may be offset from an inferior-most point of the segmentation mask 704 based on a user defined offset and/or a pre-determined distance. In the embodiment shown in FIG. 7, the inferior saturation band 718 may be approximately parallel to the dashed line of the segmentation mask 704 along the sacrum and L5 vertebra.

In this way, at least one saturation band may be generated based on curvature data (e.g., operation 606 of FIG. 6). A segmentation mask may be generated based on the diagnostic medical image to indicate an anatomy of interest (e.g., identified by the operation 604 of the method 600). At least one saturation band may be position based on anterior points and/or inferior points of the anatomy of interest (e.g., the anterior saturation band and/or the inferior saturation band). A first curvature-based threshold may be used to identify a superior region (e.g., superior vertebra) of interest used to position the anterior saturation band, and the anterior saturation band may be positioned parallel to anterior points of the superior region. The anterior saturation band may be offset from the superior region by a pre-determined (e.g., user-defined) distance. The inferior saturation band may be positioned parallel to an inferior region of the anatomy of interest based on a second curvature-based threshold and may be offset from the inferior region by a pre-determined (e.g., user-defined) distance, which may be equal to or different from the offset of the anterior saturation band from the superior region.

Additionally or alternatively, at least one saturation band may be generated based on regions of the anatomy of interest. Returning to FIG. 6, at 610, the method 600 may include generating at least one saturation band based on at least one bounding box. Briefly, this may include mapping at least one bounding box to an anatomy of interest, identifying a plane having a normal closest to a cosine direction of the segmentation mask, using cosine directions from the segmentation mask to identify a first direction of a bounding box which has a highest similarity with a second direction (e.g., opposite the first direction), adjusting a center point of the bounding box distal from the normal in either first direction or the second direction, and identifying plane parameters of the plane. Turning to FIGS. 8 and 9, a plurality of images is shown for generating saturation bands based on bounding boxes for a lower spine region, an upper spine region, and a mid-spine region.

FIG. 8 shows a plurality of segmentation mask images 800, where a segmentation mask 850 is shown for a lower spine region. A first segmentation mask image 802 indicates a lumbar spine curve of a low spine region, a second segmentation mask 804 indicates a sacral spine curve of the low spine region, and a third segmentation mask 806 shows both of the lumbar spine curve and the sacral spine curve as arranged with respect to each other in the low spine region. As described with respect to FIG. 6, the method 600 may determine that more than one saturation bands are desired for the anatomy shown in the diagnostic medical image (e.g., the lower spine region) based on anatomical landmarks. Generating at least one saturation band may include mapping at least one bounding box to the anatomy of interest, where a number of bounding boxes is equal to a desired number of saturation bands. In the embodiment shown in FIG. 8, a first bounding box 812 may be mapped to the lumbar spine curve of the low spine region and a second bounding box 814 may be mapped to the sacral spine curve of the low spine region. Voxels of the segmentation mask 850 may be on one side of a plane of a bounding box and thus be tangential to the bounding box. For example, voxels of the segmentation mask 850 which are tangential to the respective bounding box (e.g., of the first bounding box 812 and the second bounding box 814) are shown in FIG. 8 as being within the bounds of the respective bounding box. Generating a saturation band based on the bounding box includes identifying a plane of the bounding box which has a normal closest to an anterior-posterior direction of the anatomy of interest. The anterior-posterior direction may be a conventional anterior-posterior direction used when referring to an imaging subject, where a chest is anterior and a back is posterior. Left, posterior, superior (LPS) cosine directions of the segmentation mask 850 may be used to identify a plane of a bounding box having the normal closest to the anterior-posterior direction. A direction of the bounding box which has a highest cosine similarity with the posterior (P) direction may be identified as being closes to the anterior-posterior direction and a corresponding plane may be selected for generation of a saturation band. Generating a saturation band may include shifting a selected plane by half of a thickness of the respective bounding box in the normal direction.

In the embodiment shown in FIG. 8, a first plane 822 of the first bounding box 812 is determined to have a normal closest to the anterior-posterior direction of planes of the first bounding box 812. A second plane 824 of the second bounding box 814 is determined to have a normal closest to the anterior-posterior direction of planes of the second bounding box 814. A first saturation band 832 may be positioned such that the first saturation band 832 does not overlap with a region defined by the first bounding box 812 (e.g., the lumbar spine curve). A second saturation band 834 may be positioned such that the second saturation band 834 does not overlap with a region defined by the second bounding box 814.

Saturation bands may also be generated based on bounding boxes for anatomies other than the lower spine region, such as a mid-spine region and the upper spine region. Turning to FIG. 9, a plurality of segmentation masks 900 of a mid-spine region (e.g., a thoracic spine region) and an upper spine region (e.g., a cervical spine region) are shown, with corresponding saturation bands positioned adjacently. A first segmentation mask image 902 includes a thoracic segmentation mask 912 and a thoracic saturation band 922. A second segmentation mask image 904 includes a cervical segmentation mask 914 and a cervical saturation band 924. Each of the thoracic segmentation mask 912 and the cervical segmentation mask 914 may be generated based on a bounding box (not shown in FIG. 9) according to the method described with respect to FIG. 8.

Returning to operation 606, the method 600 may convert each of the at least one saturation band generated according to the methods described with respect to FIGS. 7-9, or other sufficient methods for generating saturation bands, to a ground truth plane. The ground truth plane may be equivalent to the plane projection as described with respect to FIG. 5. A position and an angulation of the ground truth plane (e.g., ground truth parameters) may equal a position and a band angulation of the corresponding saturation band, such that the ground truth plane is overlaid to align with a side of the saturation band most proximate to the anatomy of interest. In some embodiments, the ground truth plane may not be overlaid on the diagnostic medical image and instead the ground truth parameters (e.g., the position and the angulation of the ground truth plane) may be included in metadata of the diagnostic medical image to form a training data pair.

At 612, the method 600 includes outputting the diagnostic medical image and corresponding ground truth plane(s). The diagnostic medical image and corresponding ground truth plane(s), including ground truth plane parameters of position and angulation, may be output as a training data pair to an image repository or other training data repository from which training data may be sources to train a CNN to output at least one plane mask based on a localizer image input into the CNN. For example, training data pair (e.g., training data) may be stored as image data 211 on the non-transitory memory 206 of the image processing device 202 of FIG. 2B. A plurality of training data pair may be used to train the CNN implemented in the saturation band prediction workflow 100 and/or the method 300. Additionally or alternatively to the methods described with respect to FIGS. 5-9, training data may be generated using a regression network, which may be trained to predict ground-truth plane parameters, such as a position and an angulation of a ground-truth plane.

Figure 10:
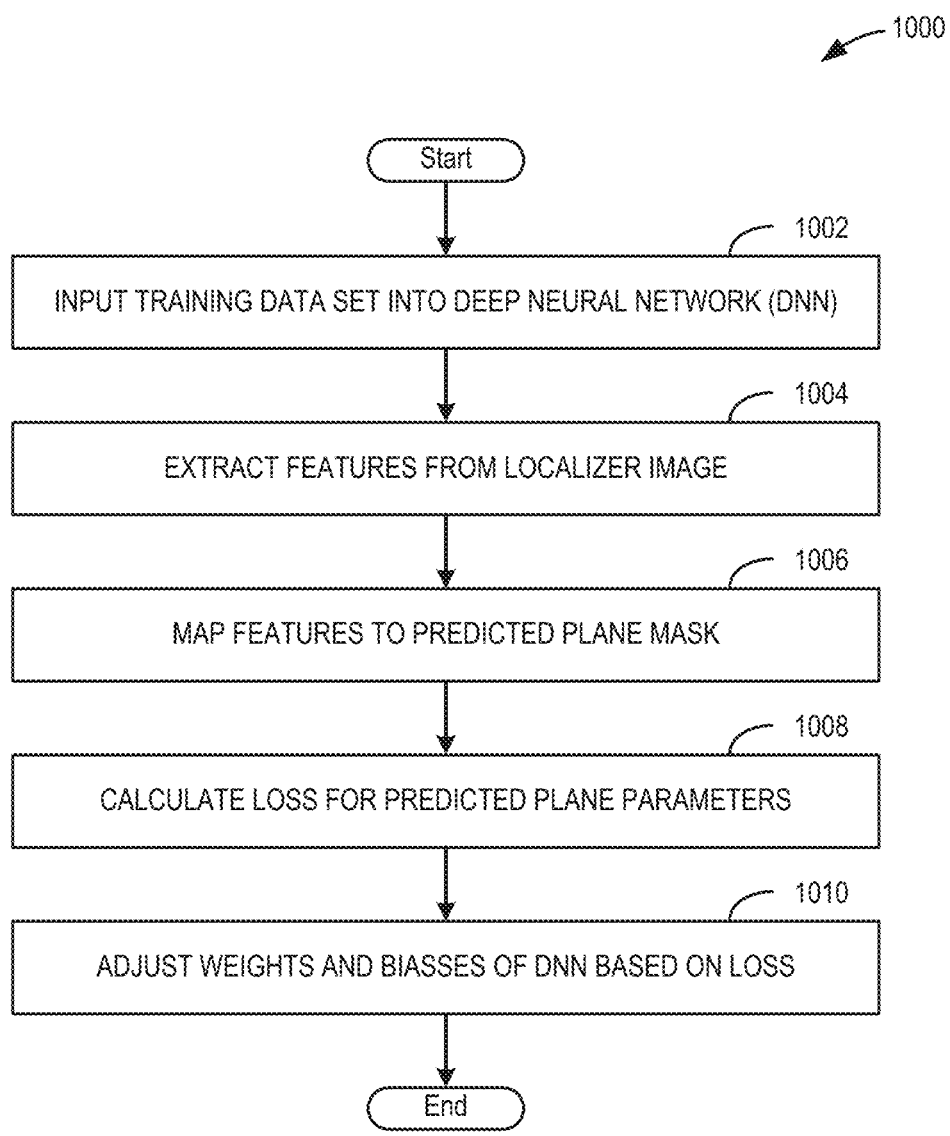
FIG. 10 is a flow chart illustrating a method for training a deep neural network to map at least one plane mask onto a localizer image, according to an exemplary embodiment.

Turning now to FIG. 10, a flow chart is shown for a method 10000 for training a deep neural network (such as a CNN implemented as described with respect to FIGS. 1 and 3) to output at least one plane mask based on a localizer image input into the CNN. The CNN may be trained using a plurality of training data pair, which may be generated according to the methods described above, or other sufficient methods for determining parameters for at least one plane based on a saturation band of a localizer image. In some embodiments, the method 1000 may be implemented by an imaging system, such as the MRI apparatus 210 of FIG. 2A, which may include the image processing device 202 of FIG. 2B. Alternatively, the method 1000 may be implemented at an image processing device not coupled to an imaging system, such as the MRI apparatus 210. The CNN may be trained at a first system (e.g., an image processing device 202) and implemented at a second system (e.g., the MRI apparatus 210).

As described above, a training data pair may include a diagnostic medical image and plane parameters for at least one plane projection generated based on a corresponding number of saturation bands for the diagnostic medical image (e.g., as described with respect to FIGS. 5-9). A plurality of training data pairs may be used to train a CNN. Briefly, a diagnostic medical image of a training data pair may be input into the untrained CNN. The untrained CNN may map a set of predicted plane parameters (e.g., at least one plane mask) based on the diagnostic medical image. A loss may be determined between the set of predicted plane parameters and plane parameters for the associated plane projection(s) of the diagnostic medical image. Weights and biases of the untrained CNN may be adjusted based on the loss. This process may be repeated for a plurality of training data pairs until loss calculated is below a desirable error threshold, at which point the CNN may be considered to be trained and may be implemented in methods for outputting at least one plane mask (e.g., and associated plane parameters) based on a localizer image.

Method 1000 begins at operation 1002, where a training data pair, from a plurality of training data pairs, is input into a deep neural network (e.g., a CNN), wherein the training data pair comprises a diagnostic medical image of an anatomical region of an imaging subject, and corresponding plane parameters for at least one plane projection indicating a position of a saturation band for the anatomical region of the diagnostic medical image. In some embodiments, the training data pair, and the plurality of training data pairs, may be stored in an imaging system, such as in image data 211 of the image processing device 202. In other embodiments, the training data pair may be acquired via communicative coupling between the imaging system and an external storage device, such as via Internet connection to a remote server.

At operation 1004, the imaging system may extract features from the diagnostic medical image using a feature extractor. In some embodiments, the feature extractor comprises one or more learnable/adjustable parameters, and in such embodiments, said parameters may be learned by execution of method 1000. In some embodiments, the feature extractor comprises hard-coded parameters, and does not include learnable/adjustable parameters, and in such embodiments the feature extractor is not trained during execution of method 1000. In other embodiments, the imaging system may identify anatomies of the diagnostic medical image by prescribing a segmentation mask to the diagnostic medical image, as described with respect to FIGS. 5-9.

At operation 1006, the imaging system maps the features to at least one predicted plane mask for the anatomy of interest identified at operation 1004, using a deep neural network. In some embodiments, the deep neural network comprises a CNN, comprising one or more convolutional layers, comprising one more convolutional filters. The deep neural network maps the features to a predicted plane mask by propagating the features from the input layer, through one or more hidden layers, until reaching an output layer of the deep neural network. The predicted plane mask may include associated predicted plane parameters, including a position and an angulation of the plane mask. The predicted plane mask may be a 3D projection on the diagnostic medical image to identify a plane adjacent to the anatomy of interest.

At operation 1008, the imaging system calculates a loss for the predicted plane parameters (e.g., of each predicted plane mask of the at least one plane mask) based on a difference between the predicted plane parameters and the ground truth plane parameters (e.g., the plane parameters of the diagnostic medical image included in the training data pair). In one embodiment, the loss comprises a mean-squared-error, given by the following equation:

$$MSE = \frac{1}{N}\sum_{i=0}^{N}(x_i - X_i)^2$$

Where MSE stands for mean-squared-error, N is the total number of training data pairs, i is an index indicating the currently selected training data pair, $x_i$ is a predicted thickness mask for training data pair i, and $X_i$ is a ground truth thickness mask for training data pair i. The expression $x_i$-$X_i$ will be understood to represent pair-wise subtraction of each pair of corresponding thickness values in the predicted thickness mask and the ground truth thickness mask, for the currently selected training data pair i. It will be appreciated that other loss functions known in the art of machine learning may be employed at operation 1008.

At operation 1010, the weights and biases of the deep neural network are adjusted based on the loss determined at operation 1008. In some embodiments, the parameters of the feature extractor, and the CNN, may be adjusted to reduce the loss over a set of training data pair. In some embodiments, the feature extractor may not include a learnable parameter, and therefore operation 1010 may not include adjusting parameters of the feature extractor. In some embodiments, back propagation of the loss may occur according to a gradient descent algorithm, wherein a gradient of the loss function (a first derivative, or approximation of the first derivative) is determined for each weight and bias of the deep neural network. Each weight (and bias) of the deep neural network is then updated by adding the negative of the product of the gradient determined (or approximated) for the weight (or bias) with a predetermined step size. Method 1000 may then end. It will be noted that method 1000 may be repeated for each of a plurality of training data pairs in a training data set, and this process may be repeated until a stop condition is met. Wherein, in some embodiments, the stop condition comprises one or more of the loss decreasing to below a threshold loss, a rate of loss change decreasing to below a threshold rate of loss change, a validation loss, determined over a validation data set, reaching a minimum, and so on. In this way, a CNN may learn to map said at least one plane mask to an anatomy of interest for a diagnostic medical image.

As described herein, training data pairs including a diagnostic medical image and plane parameters based on desired saturation bands for the diagnostic medical image may be generated, and the generated training data pairs may be used to train a deep neural network, such as a CNN, to output at least one plane mask based on a localizer image input into the CNN. Each of the at least one plane mask may be a 3D projection indicating a plane adjacent to an anatomy of interest. A plane mask may indicate a band position and a band angulation at which a saturation band may be placed on the diagnostic medical image. A graphical prescription including at least one saturation band based on a corresponding number of plane masks may be output for display on a display device. Following optional adjustment by a user, a diagnostic scan may be performed using a MRI apparatus, in which saturation pulses are directed to regions indicated by the at least one saturation band. Identifying the at least one saturation band (e.g., a 2D plane overlaid on the diagnostic medical image) based on a corresponding plane mask (e.g., a 3D projection) may allow for consistent imaging data to be captured over multiple scans longitudinally. The plane mask may identify a 3D plane and therefore allow for consistent saturation band placement, where the saturation band may be positioned based on the plane mask and sufficiently suppress signals in a region covered by the saturation band, irrespective of patient pose. A duration of image capture as well as a level of user error may decrease, as automated prescription of at least one saturation band may decrease user input during image capture.

Automatic placement of a saturation band on a localizer image at a position and an angulation of a plane mask, where the plane mask is generated by a deep neural network based on the localizer image, may allow for more consistency and accuracy in saturation band placement. This may provide consistency in diagnostic images captured based on graphical prescriptions including at least one saturation band overlaid on the image, where the at least one saturation band indicates a region where it is desired to apply a saturation pulse and therefore suppress signal from underlying anatomy. Additionally, automatic positioning of the saturation band based on the plane mask may improve processing efficiency of diagnostic image generation. For example, training a deep neural network, such as a CNN as described herein, to identify a position and an angulation of a plane at an anterior-most or inferior-most point of an anatomy of interest may provide a method for generating at least one plane mask based on the anatomy of interest for multiple different anatomies using less data and with faster processing than conventional approaches. Other image processing methods may include identifying saturation band position and angulation based on a specific anatomy, for example, positioning a saturation band for an upper spine region at a first location, where the first location is predetermined and prescription of the saturation band is contingent on positioning of the anatomy of interest (e.g., the upper spine region) in an imaging region. This may not account for the anatomy of interest as a 3D image, as the saturation band is a 2D projection on the localizer image. Instead, using the position and the angulation of the plane mask to position the saturation band may allow for the saturation band to be positioned with respect to the anatomy of interest as a 3D image and potential differences in the anatomy of interest (e.g., lesions, foreign objects, and so on) which may provide challenges to placement of the saturation band based on a predetermined position. The systems and methods described herein may improve processing efficiency for placement of at least one saturation band. Using a trained deep neural network to generate a plane mask based on a localizer image and placing a saturation band based on placement of the plane mask provides an efficient method for determining, via more efficient calculations, saturation band position. Processing efficiency of automated placement of at least one saturation band may thus be improved. For example, because the saturation band placement position and/or orientation may be impacted by complex geometrical considerations, basing the determining on the mask enables the processing by the processor to be faster and more efficient. Further, by using the trained network to generate the mask of the localizer image, and then determining the saturation based on the band, a more efficient approach is used where less data is processed and less complex algorithms may be implemented on the processor in order to generate the saturation band.

The disclosure also provides support for a method, comprising: acquiring a localizer image of an imaging subject, determining a plane mask for the localizer image by entering the localizer image as input to a deep neural network trained to output the plane mask based on the localizer image, generating a saturation band based on the plane mask by positioning the saturation band at a position and an angulation of the plane mask, and outputting a graphical prescription for display on a display device, the graphical prescription including the saturation band overlaid on the localizer image. In a first example of the method, the plane mask is a projection of a plane of a 3D coordinate system onto the localizer image. In a second example of the method, optionally including the first example, overlaying the saturation band on the localizer image includes positioning the saturation band at the position and the angulation of the plane mask. In a third example of the method, optionally including one or both of the first and second examples, at least one of a position and an angulation of the saturation band are determined based on plane fitting plane parameters of the plane mask. In a fourth example of the method, optionally including one or more or each of the first through third examples, the method further comprises: determining a width of the saturation band in response to input received from a user input device. In a fifth example of the method, optionally including one or more or each of the first through fourth examples, the method further comprises: adjusting the graphical prescription, including at least one of a position, an angulation, and a width of the saturation band, based on user input. In a sixth example of the method, optionally including one or more or each of the first through fifth examples, the method further comprises: performing a diagnostic scan of the imaging subject according to the graphical prescription, including performing one or more saturation pulses at a location dictated by the saturation band.

The disclosure also provides support for a method, comprising: acquiring a medical image, labeling the medical image with ground truth parameters, mapping predicted plane parameters to the medical image using a deep neural network, comparing the predicted plane parameters with the ground truth parameters and computing loss based on a difference between the predicted plane parameters and the ground truth parameters, and adjusting weights and biases of the deep neural network based on loss to train the deep neural network to output a plane projection based on a medical image input into the deep neural network. In a first example of the method, the plane projection is a projection of a plane where a 3D coordinate system and an image plane of the medical image intersect. In a second example of the method, optionally including the first example, the ground truth parameters include a plane position and a plane angulation of the plane projection. In a third example of the method, optionally including one or both of the first and second examples, determining at least one of the plane position and the plane angulation includes training a regression network and implementing the regression network to identify at least one of the plane position and the plane angulation based on the medical image. In a fourth example of the method, optionally including one or more or each of the first through third examples, determining at least one of the plane position and the plane angulation includes: acquiring the medical image, generating a saturation band based on the medical image, and determining the plane position and the plane angulation based on a band position and a band angulation of the saturation band, respectively. In a fifth example of the method, optionally including one or more or each of the first through fourth examples, generating the saturation band includes generating a segmentation mask of the medical image to identify an anatomy of interest of the medical image. In a sixth example of the method, optionally including one or more or each of the first through fifth examples, the anatomy of interest includes at least one curvature. In a seventh example of the method, optionally including one or more or each of the first through sixth examples, generating the saturation band for the anatomy of interest includes: identifying a first curvature of the anatomy of interest using a first curvature-based threshold, fitting a first plane to anterior points of the first curvature, and positioning an anterior saturation band parallel to and offset from the first plane by a pre-determined distance. In an eighth example of the method, optionally including one or more or each of the first through seventh examples, generating the saturation band for the anatomy of interest further includes: identifying a second curvature of the anatomy of interest using a second curvature-based threshold, fitting a second plane to inferior points of the second curvature, and positioning an inferior saturation band parallel to and offset from the second plane by a pre-determined distance. In a ninth example of the method, optionally including one or more or each of the first through eighth examples, generating the saturation band comprises: mapping at least one bounding box to the anatomy of interest, identifying the plane having a normal closest to a direction of the segmentation mask, using left, posterior, superior (LPS) cosine directions from the segmentation mask to identify a first direction of a bounding box which has a highest similarity with a second direction, opposite the first direction, adjusting a center point of the bounding box distal from the normal in either first direction or the second direction, and identifying plane parameters of the plane. In a tenth example of the method, optionally including one or more or each of the first through ninth examples, each of the at least one bounding boxes are mapped to anatomical landmarks of the anatomy of interest. In an eleventh example of the method, optionally including one or more or each of the first through tenth examples, the deep neural network comprises a plurality of convolutional filters, wherein a sensitivity of each of the plurality of convolutional filters is modulated by a corresponding spatial regularization factor.

The disclosure also provides support for an imaging system comprising: an imaging device, a memory, storing: a trained convolutional neural network (CNN), and instructions, a display device, and a processor communicably coupled to the imaging device, the display device, and the memory, and when executing the instructions, configured to: acquire a medical image of an imaging subject via the imaging device, map a plane mask for the imaging subject using the trained CNN, generate a saturation band based on the plane mask, and display a graphical prescription on the display device, the graphical prescription including the saturation band overlaid on the medical image.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:
   acquiring a localizer image of an imaging subject;
   determining a plane mask for the localizer image by entering the localizer image as input to a deep neural network trained to output the plane mask based on the localizer image, the plane mask indicating a location, relative to the localizer image, of a plane of a saturation band to be positioned;
   positioning the saturation band based on the plane mask by positioning the saturation band at a position and an angulation of the plane indicated by the plane mask; and
   outputting a graphical prescription for display on a display device, the graphical prescription including a depiction of the saturation band overlaid on the localizer image.

2. The method of claim 1, wherein the location of the plane in the plane mask is where a projection of the plane in a 3D coordinate system intersects the localizer image.

3. The method of claim 1, wherein the plane mask is a binary segmentation mask having spatial correspondence to the localizer image that identifies the location of the plane with a matrix of first values and second values, wherein each first value indicates a corresponding first pixel of the localizer image belongs to an object class of interest and each second value indicates a corresponding second pixel of the localizer image does not belong to the object class of interest.

4. The method of claim 1, further comprising determining a width of the saturation band in response to input received from a user input device.

5. The method of claim 1, further comprising adjusting the graphical prescription, including at least one of a position, an angulation, and a width of the saturation band, based on user input.

6. The method of claim 1, further comprising performing a diagnostic scan of the imaging subject according to the graphical prescription, including performing one or more saturation pulses at a location dictated by the saturation band, and wherein the plane mask is visualized as a line on the localizer image.

7. An imaging system comprising:
   an imaging device;
   a memory, storing:
      a trained convolutional neural network (CNN); and
      instructions;
   a display device; and
   a processor communicably coupled to the imaging device, the display device, and the memory, and when executing the instructions, configured to:
      acquire a medical image of an imaging subject via the imaging device;
      map a plane mask for the imaging subject using the trained CNN and the medical image, the plane mask identifying a plane of a saturation band to be positioned;
      position the saturation band based on the plane mask; and
      display a graphical prescription on the display device, the graphical prescription including a depiction of the saturation band overlaid on the medical image.

8. The method of claim 1, wherein the deep neural network is trained with training data pairs, each training data pair including a training localizer image and an associated ground truth.

9. The method of claim 8, wherein the associated ground truth includes a set of plane parameters for a training plane of a training saturation band, including a plane position and a plane angulation, or the associated ground truth includes a graphical depiction of the training plane on the training localizer image.

* * * * *